(12) United States Patent
Naidu

(10) Patent No.: US 7,897,592 B2
(45) Date of Patent: Mar. 1, 2011

(54) HIV INTEGRASE INHIBITORS

(75) Inventor: B. Narasimhulu Naidu, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 900 days.

(21) Appl. No.: 11/599,580

(22) Filed: Nov. 14, 2006

(65) Prior Publication Data

US 2007/0112190 A1 May 17, 2007

Related U.S. Application Data

(60) Provisional application No. 60/736,964, filed on Nov. 15, 2005.

(51) Int. Cl.
*A61P 31/00* (2006.01)
*A61K 31/54* (2006.01)
*A61K 31/55* (2006.01)
*C07D 513/00* (2006.01)

(52) U.S. Cl. .............. 514/210.02; 514/210.21; 514/212.08; 514/224.2; 540/524; 544/48

(58) Field of Classification Search ............ 514/210.02, 514/210.21, 212.08, 224.2; 540/524; 544/48
See application file for complete search history.

(56) References Cited

U.S. PATENT DOCUMENTS

2006/0046985 A1    3/2006   Crescenzi et al.

FOREIGN PATENT DOCUMENTS

| EP | 1698628 A1 | 9/2006 |
|---|---|---|
| WO | WO 2005/061490 A1 | 7/2005 |
| WO | WO 2005/061501 A2 | 7/2005 |
| WO | WO 2006/103399 A1 | 10/2006 |
| WO | WO 2006/121831 A2 | 11/2006 |

OTHER PUBLICATIONS

U.S. Appl. No. 11/599,580, filed Nov. 14, 2006, B. Narasimhulu Naidu.
U.S. Appl. No. 60/817,009, filed Jun. 28, 2006, Michael A. Walker, et al.
U.S. Appl. No. 11/511,751, filed Aug. 29, 2006, Jacques Banville, et al.
U.S. Appl. No. 11/138,773, filed May 26, 2005, B. Narasimhulu Naidu, et al.
U.S. Appl. No. 11/138,726, filed May 26, 2005, Jacques Banville, et al.
U.S. Appl. No. 11/126,891, filed May 11, 2005, B. Narasimhulu Naidu, et al.
U.S. Appl. No. 11/288,533, filed Nov. 29, 2005, B. Narasimhulu Naidu, et al.
U.S. Appl. No. 11/110,589, filed Apr. 20, 2005, B. Narasimhulu Naidu.
U.S. Appl. No. 11/273,671, filed Nov. 14, 2005, B. Narasimhulu Naidu.

*Primary Examiner*—Brenda L Coleman
(74) *Attorney, Agent, or Firm*—James Epperson

(57) ABSTRACT

The invention encompasses a series bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

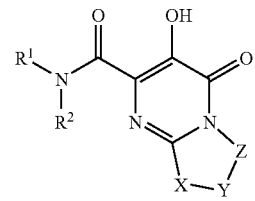

17 Claims, No Drawings

HIV INTEGRASE INHIBITORS

CROSS REFERENCE TO RELATED APPLICATIONS

This application claims the benefit of U.S. provisional application Ser. No. 60/736,964 filed Nov. 15, 2005.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host-bell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

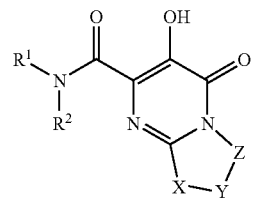

wherein:
$R^1$ is $(Ar^1)$alkyl, $(Ar^1)(CON(R^8)(R^9))$alkyl, $(Ar^1)(CO_2R^{14})$alkyl, $(Ar^1)$hydroxyallkyl, or $(Ar^1)$oxyalkyl;
$R^2$ is hydrogen, alkyl, hydroxy, or alkoxy;
$R^3$ is hydrogen, halo, hydroxy, cyano, alkyl, cycloalkyl, $C_{5-7}$cycloalkenyl, haloalkyl, alkoxy, alkylthio, haloalkoxy, $N(R^8)(R^9)$, $NHAr^2$, $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=N)R^7$, $SO_2R^7$, $SO_2N(R^6)(R^6)$, $PO(OR^6)_2$, $C_{2-4}(R^{12})$alkynyl, $R^{13}$, $Ar^2$, or $Ar^3$;
$R^4$ is hydrogen, halo, hydroxy, cyano, alkyl, alkoxy, haloalkyl, haloalkoxy, or $N(R^6)(R^6)$;
$R^5$ is hydrogen, halo, hydroxy, cyano, alkyl, alkoxy, haloalkyl, haloalkoxy, or $N(R^6)(R^6)$;
$R^6$ is hydrogen, alkyl, or cycloalkyl;
$R^7$ is alkyl or cycloalkyl;
$R^8$ is hydrogen, alkyl, hydroxyalkyl, alkoxyalkyl or dialkylaminoalkyl;
$R^9$ is hydrogen, alkyl, hydroxyalkyl, alkoxyalkyl or dialkylaminoalkyl; or
$N(R^8)(R^9)$ taken together is azetidinyl, pyrrolidinyl, $(R^{10})$-piperidinyl, $N-(R^{11})$-piperazinyl, morpholinyl, thiomorpholinyl, or dioxothiazinyl;
$R^{10}$ is hydrogen, alkyl, or hydroxyalkyl;
$R^{11}$ is hydrogen, alkyl, cycloalkyl, $COR^6$, or $CO_2R^6$;
$R^{12}$ is hydrogen, hydroxy, $N(R^6)(R^6)$, $SO_2R^7$, $OSO_2R^7$, or dioxothiazinyl;
$R^{13}$ is azetidinonyl, pyrrolidinonyl, valerolactamyl, caprolactamyl, maleimido, oxazolidonyl, or dioxothiazinyl, and is substituted with 0-2 substituents selected from the group consisting of alkyl, hydroxyalkyl, acetoxyalkyl, and aminoalkyl;
$R^{14}$ is hydrogen or alkyl;

or two R¹⁴'s taken together are CH₂CH₂, CH₂CH₂CH₂, CH₂CH₂CH₂CH₂, CH₂CH₂CH₂CH₂CH₂, CH₂CH₂CH₂CH₂CH₂CH₂, OCH₂CH₂, CH₂CH₂, OCH₂CH₂CH₂, CH₂OCH₂CH₂, OCH₂CH₂CH₂CH₂, CH₂OCH₂CH₂CH₂, CH₂CH₂OCH₂CH₂, OCH₂CH₂CH₂CH₂CH₂, CH₂OCH₂CH₂CH₂CH₂, CH₂CH₂OCH₂CH₂CH₂, N(R⁶)CH₂CH₂, CH₂N(R⁶)CH₂, N(R⁶)CH₂CH₂CH₂, CH₂N(R⁶)CH₂CH₂, N(R⁶)CH₂CH₂CH₂CH₂, CH₂N(R⁶)CH₂CH₂CH₂, CH₂CH₂N(R⁶)CH₂CH₂, N(R⁶)CH₂CH₂CH₂CH₂CH₂, CH₂N(R⁶)CH₂CH₂CH₂CH₂, or CH₂CH₂N(R⁶)CH₂CH₂CH₂, provided that the two R¹⁴'s are attached to a common carbon atom;

[Ar¹ structural diagrams shown]

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, N(R⁸)(R⁹), CON(R⁸)(R⁹), CO₂R⁶, CONHSO₂N(R⁶)(R⁶), CONHSO₂N(R⁶)(phenyl), and CONHSO₂N(R⁶)(halophenyl);

Ar³ is phenyl substituted with 0-2 substituents selected from the group consisting of halo, cyano, hydroxy, alkyl, alkoxy, alkoxyalkyl, haloalkyl, haloalkoxy, N(R⁸)(R⁹), CON(R⁶)(R⁶), and CH₂N(R⁸)(R⁹), or is dioxolanylphenyl; and X-Y-Z is X-Y-Z is C(R¹⁴)₂SC(R¹⁴)₂, C(R¹⁴)₂SC(R¹⁴)₂C(R¹⁴)₂, C(R¹⁴)₂SC(R¹⁴)₂C(R¹⁴)₂C(R¹⁴)₂, C(R¹⁴)₂SOC(R¹⁴)₂, C(R¹⁴)₂SOC(R¹⁴)₂C(R¹⁴)₂, C(R¹⁴)₂SOC(R¹⁴)₂C(R¹⁴)₂C(R¹⁴)₂, C(R¹⁴)₂SO₂C(R¹⁴)₂, C(R¹⁴)₂SO₂C(R¹⁴)₂C(R¹⁴)₂, or C(R¹⁴)₂SO₂C(R¹⁴)₂C(R¹⁴)₂C(R¹⁴)₂;

or a pharmaceutically acceptable salt thereof.

Another aspect of the invention is a compound of Formula I

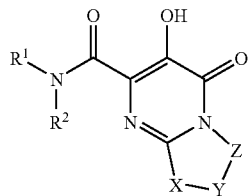

wherein:

$R^1$ is $(Ar^1)$alkyl, $(Ar^1)(CON(R^8)(R^9))$alkyl, $(Ar^1)(CO_2R^{14})$alkyl, $(Ar^1)$hydroxyalkyl, or $(Ar^1)$oxyalkyl;

$R^2$ is hydrogen, alkyl, hydroxy, or alkoxy;

$R^3$ is hydrogen, halo, hydroxy, cyano, alkyl, cycloalkyl, $C_{5-7}$cycloalkenyl, haloalkyl, alkoxy, alkylthio, haloalkoxy, $N(R^8)(R^9)$, $NHAr^2$, $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=N)R^7$, $SO_2R^7$, $SO_2N(R^6)(R^6)$, $PO(OR^6)_2$, $C_{2-4}(R^{12})$alkynyl, $R^{13}$, $Ar^2$, or $Ar^3$;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, or cycloalkyl;

$R^7$ is alkyl or cycloalkyl;

$R^8$ is hydrogen, alkyl, hydroxyalkyl, alkoxyalkyl or dialkylaminoalkyl;

$R^9$ is hydrogen, alkyl, hydroxyalkyl, alkoxyalkyl or dialkylaminoalkyl; or $N(R^8)(R^9)$ taken together is azetidinyl, pyrrolidinyl, $(R^{10})$-piperidinyl, $N-(R^{11})$-piperazinyl, morpholinyl, thiomorpholinyl, or dioxothiazinyl;

$R^{10}$ is hydrogen, alkyl, or hydroxyalkyl;

$R^{11}$ is hydrogen, alkyl, cycloalkyl, $COR^6$, or $CO_2R^6$;

$R^{12}$ is hydrogen, hydroxy, $N(R^6)(R^6)$, $SO_2R^7$, $OSO_2R^7$, or dioxothiazinyl;

$R^{13}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

$R^{14}$ is hydrogen or alkyl;

or two R¹⁴'s taken together are CH₂CH₂, CH₂CH₂CH₂, CH₂CH₂CH₂CH₂, CH₂CH₂CH₂CH₂CH₂, CH₂CH₂CH₂CH₂CH₂CH₂, OCH₂CH₂, CH₂OCH₂, OCH₂CH₂CH₂, CH₂OCH₂CH₂, OCH₂CH₂CH₂CH₂, CH₂OCH₂CH₂CH₂, CH₂CH₂OCH₂CH₂, OCH₂CH₂CH₂CH₂CH₂, CH₂OCH₂CH₂CH₂CH₂, CH₂CH₂OCH₂CH₂CH₂, N(R⁶)CH₂CH₂, CH₂N(R⁶)CH₂, N(R⁶)CH₂CH₂CH₂, CH₂N(R⁶)CH₂CH₂, N(R⁶)CH₂CH₂CH₂CH₂, CH₂N(R⁶)CH₂CH₂CH₂, CH₂CH₂N(R⁶)CH₂CH₂, N(R⁶)CH₂CH₂CH₂CH₂CH₂, CH₂N(R⁶)CH₂CH₂CH₂CH₂, or CH₂CH₂N(R⁶)CH₂CH₂CH₂, provided that the two R¹⁴'s are attached to a common carbon atom;

Ar¹ is 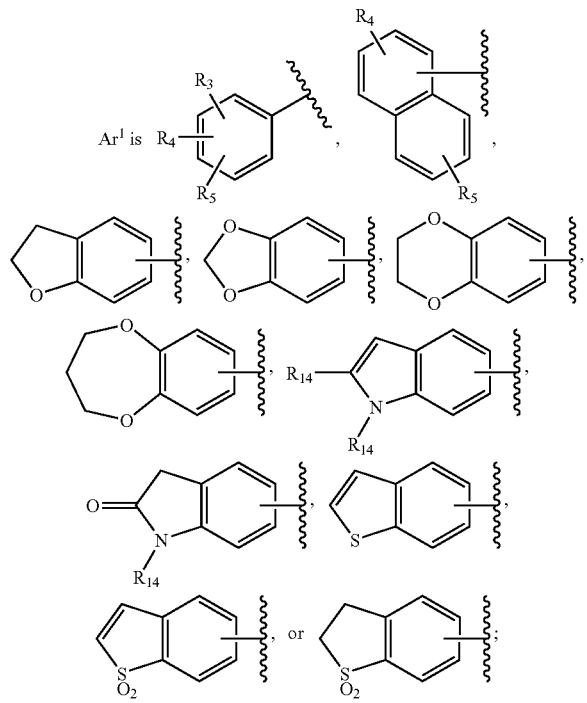

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, $N(R^8)(R^9)$, $CON(R^8)(R^9)$, $CO_2R^6$, $CONHSO_2N(R^6)(R^6)$, $CONHSO_2N(R^6)$(phenyl), and $CONHSO_2N(R^6)$(halophenyl);

Ar³ is phenyl substituted with 0-2 substituents selected from the group consisting of halo, cyano, hydroxy, alkyl, alkoxy, alkoxyalkyl, haloalkyl, haloalkoxy, $N(R^8)(R^9)$, $CON(R^6)(R^6)$, and $CH_2N(R^8)(R^9)$, or is dioxolanylphenyl; and X-Y-Z is X-Y-Z is $C(R^{14})_2SC(R^{14})_2$, $C(R^{14})_2SC(R^{14})_2C(R^{14})_2$, $C(R^{14})_2SC(R^{14})_2C(R^{14})_2C(R^{14})_2$, $C(R^{14})_2SOC(R^{14})_2$, $C(R^{14})_2SOC(R^{14})_2C(R^{14})_2$, $C(R^{14})_2SOC(R^{14})_2C(R^{14})_2C(R^{14})_2$, $C(R^{14})_2SO_2C(R^{14})_2$, $C(R^{14})_2SO_2C(R^{14})_2C(R^{14})_2$, or $C(R^{14})_2SO_2C(R^{14})_2C(R^{14})_2C(R^{14})_2$;

or a pharmaceutically acceptable salt thereof.

Another aspect of the invention is a compound of Formula I where R¹ is (Ar¹)alkyl.

Another aspect of the invention is a compound of Formula I where R¹ is

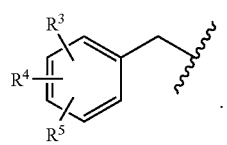

Another aspect of the invention is a compound of Formula I where R¹ is

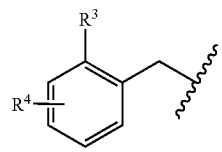

and R³ is other than hydrogen or halo.

Another aspect of the invention is a compound of Formula I where R² is hydrogen.

Another aspect of the invention is a compound of Formula I where R³ is $N(R^8)(R^9)$, $N(R^6)COR^7$, $OCON(R^8)(R^9)$, $CON(R^8)(R^9)$, $SOR^7$, $SO_2R^7$, $SO_2N(R^6)(R^6)$, $PO(OR^6)_2$, $R^{13}$, or Ar².

Another aspect of the invention is a compound of Formula I where R³ is $R^{13}$.

Another aspect of the invention is a compound of Formula I where R³ is Ar².

Another aspect of the invention is a compound of Formula I where Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of halo and alkyl.

Another aspect of the invention is a compound of Formula I where X-Y-Z is $C(R^{14})_2SCH_2$, $C(R^{14})_2SCH_2CH_2$, $C(R^{14})_2SCH_2CH_2CH_2$, $C(R^{14})_2SO_2CH_2$, $C(R^{14})_2SO_2CH_2CH_2$, or $C(R^{14})_2SO_2CH_2CH_2CH_2$.

Another aspect of the invention is a compound of Formula I where X-Y-Z is $C(R^{14})_2SCH_2$, $C(R^{14})_2SCH_2CH_2$, $C(R^{14})_2SCH_2CH_2CH_2$, $C(R^{14})_2SO_2CH_2$, $C(R^{14})_2SO_2CH_2CH_2$, or $C(R^{14})_2SO_2CH_2CH_2CH_2$, and $R^{14}$ is other than hydrogen.

Another aspect of the invention is a compound of Formula I according to one of the following structures.

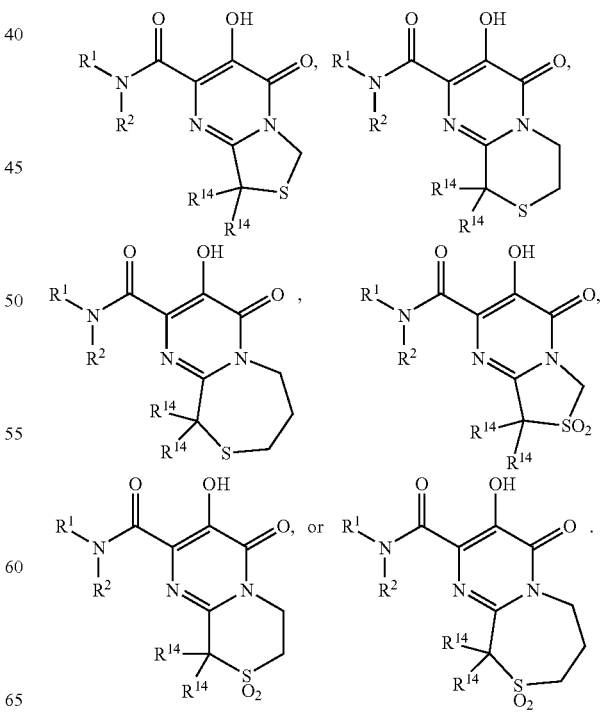

Another aspect of the invention is a compound of Formula I according to one of the following structures.

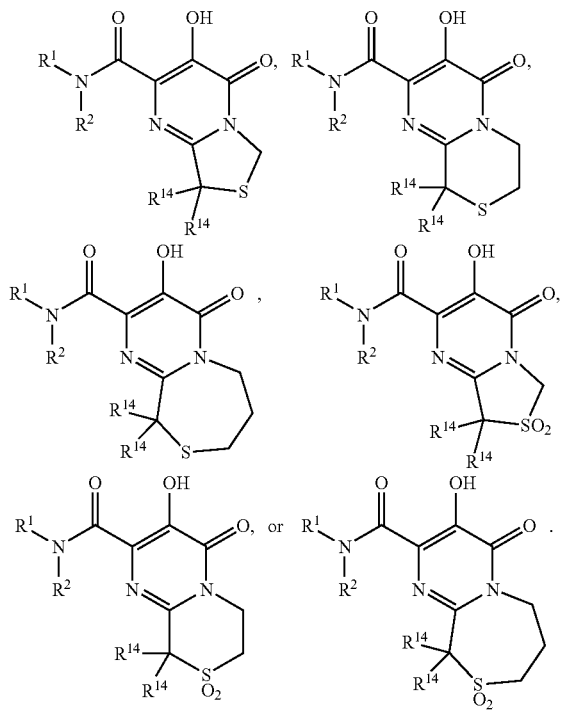

and R$^{14}$ is other than hydrogen.

Another aspect of the invention is a compound of Formula I where R$^{14}$ is methyl.

Another aspect of the invention is a compound of Formula I where two R$^{14}$'s taken together are CH$_2$CH$_2$, CH$_2$CH$_2$CH$_2$, CH$_2$CH$_2$CH$_2$CH$_2$, CH$_2$CH$_2$CH$_2$CH$_2$CH$_2$, CH$_2$CH$_2$CH$_2$CH$_2$CH$_2$CH$_2$, CH$_2$OCH$_2$CH$_2$, CH$_2$OCH$_2$CH$_2$CH$_2$, CH$_2$CH$_2$OCH$_2$CH$_2$, CH$_2$OCH$_2$CH$_2$CH$_2$CH$_2$, CH$_2$CH$_2$OCH$_2$CH$_2$CH$_2$, CH$_2$CH$_2$NHCH$_2$CH$_2$, or CH$_2$CH$_2$N(CH$_3$)CH$_2$CH$_2$, provided that the two R$^{14}$'s are attached to a common carbon.

For a compound of Formula I, any scope of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, Ar$^1$, Ar$^2$, Ar$^3$, and X-Y-Z can be used independently with any scope of any other substituent. Each instance of a variable is independent of another instance.

Unless specified otherwise, these terms have the following meanings. "Alkyl" means a straight or branched alkyl group composed of 1 to 6 carbons. "Alkenyl" means a straight or branched alkenyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from mono-halo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

"(Ar$^1$)oxyalkyl" means Ar$^1$ is attached at the oxygen.

"Dioxolanyphenyl" means

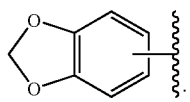

"Dioxothiazinyl" means

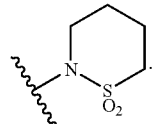

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

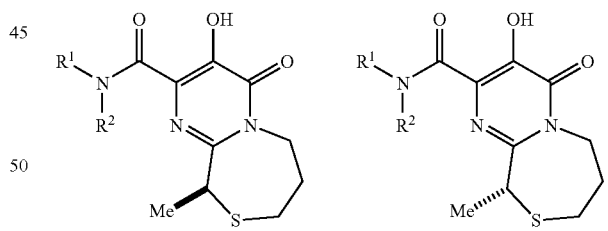

The invention includes all tautomeric forms of the compounds. An example of a tautomeric pair is shown below.

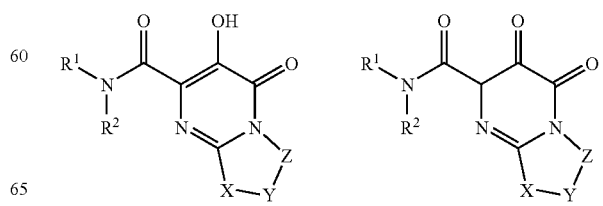

Synthetic Methods

The compounds of this invention can be made by various methods known in the art including those of the following schemes and in the specific, embodiments section. The variable numbering and structure numbering shown in the synthetic schemes are distinct from, and should not be confused with, the variables or structure numbering in the claims or the rest of the specification. The variables in the schemes are meant only to illustrate how to make some of the compounds of this invention.

Some compounds can be synthesized from an appropriately substituted heterocycle I-1 according to Scheme I, where $R_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis ($H_2$—Pd/C) or acid hydrolysis (trifluoroacetic acid) to yield intermediate I-2. I-2 can be transaminated to I-4 by reaction with amine I-3. In a number of cases this reaction can be carried out by heating I-3 and I-2 together in the presence of base. Alternatively, standard amide coupling reagents can be used to effect the formation of the amide bond. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as BOP, DCC, EDCI, PyBrop, PyBop or other reagents (see March, J. Advanced Organic Chemistry, Fourth Edition 1992 John Wiley & Sons, New York). The resulting intermediate I-6 can be deprotected as described for intermediate I-1.

In Scheme II, intermediate II-3 can be prepared using methods similar to those described in Sunderland, J. S.; Botta, M.; Aime, S.; Raymond, K. N. Inorg. Chem. (2001), 40, 6756-6756, where II-1 and II-2 are condensed, to provide intermediate II-3. This reaction is usually conducted in the presence of a base such as sodium hydride (NaH), sodium ethoxide (EtONa) or lithium hexamethyldisilazide (LiHMDS). Using the methods described in the reference, II-3 can be condensed with an appropriately substituted amidine II-4 to form II-5. Substituent B can be a leaving group, such as -halo (Cl, Br or I) or can be converted to a leaving group under appropriate conditions such as by forming the corresponding methylsulfonate ester. When substituent B is a methyl sulphide group it can be treated with iodomethane to form a dimethylsulfonium intermediate which is activated towards nucleophilic attack to effect ring closure.

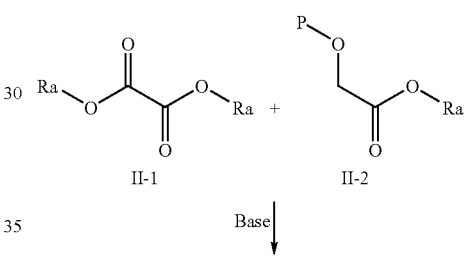

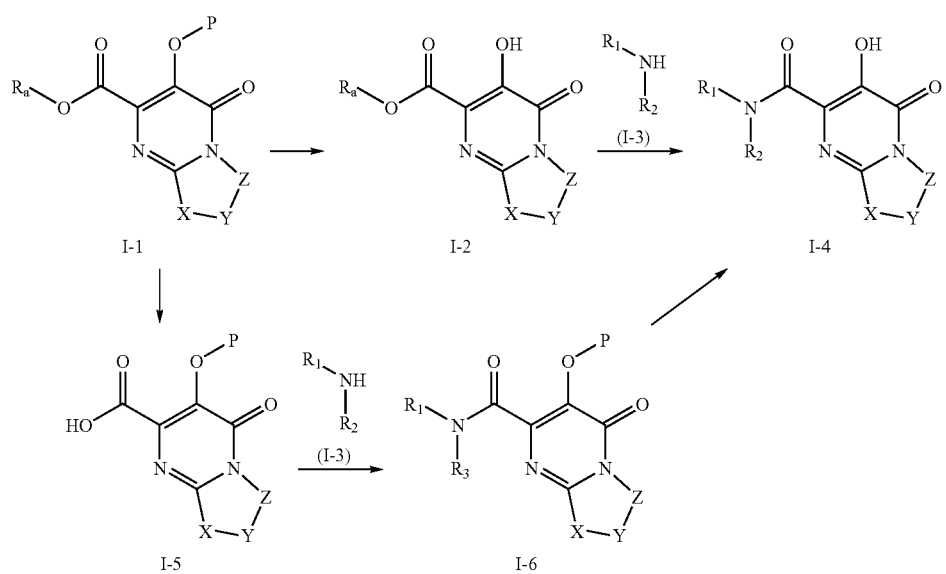

mediate IV-2. This intermediate can be reacted with a suitably protected alkyne to form IV-3 which can rearrange to from intermediate IV-4 according to literature methods (Culbertson, T. P. *Journal of Heterocyclic Chemistry*, 1979, 16, 1423-1424).

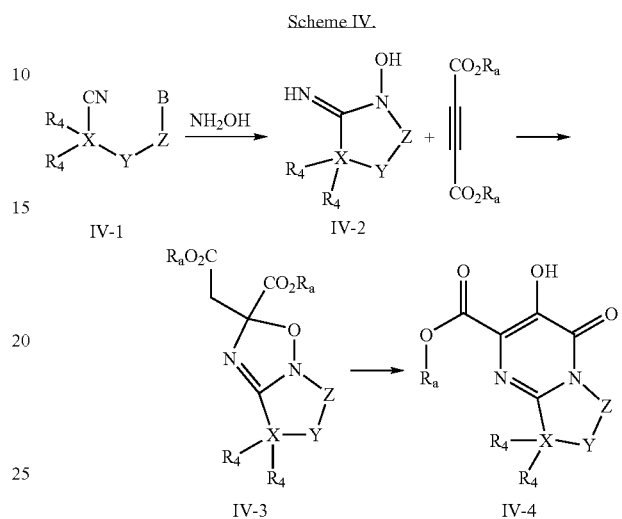

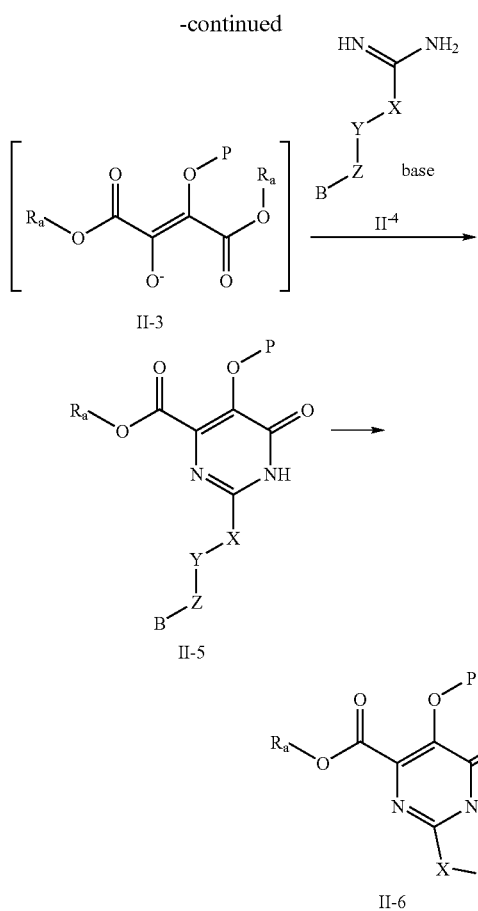

In Scheme III, intermediate II-3 can be condensed with a cyclic-amidine to yield intermediate I-1. Intermediate III-1 can be prepared using known methods (see Patai, S. and Rappoport, Z. The Chemistry of Amidines and Imidates, Volume 2, 1991, John Wiley & Sons, New York).

Another method is illustrated in Scheme V. This synthetic path begins with an appropriately substituted ketone which can be transformed to the corresponding nitrile intermediate V-1. This in turn can be reacted with 2-mercaptoethanol followed by thionyl chloride to produce compound V-2, which can be reacted with hydroxylamine and an acetylene dicarboxylate ester to yield intermediate V-4. Heating of the intermediate can yield intermediate V-5. Synthesis of the corresponding amide derivatives can be accomplished according to Scheme I.

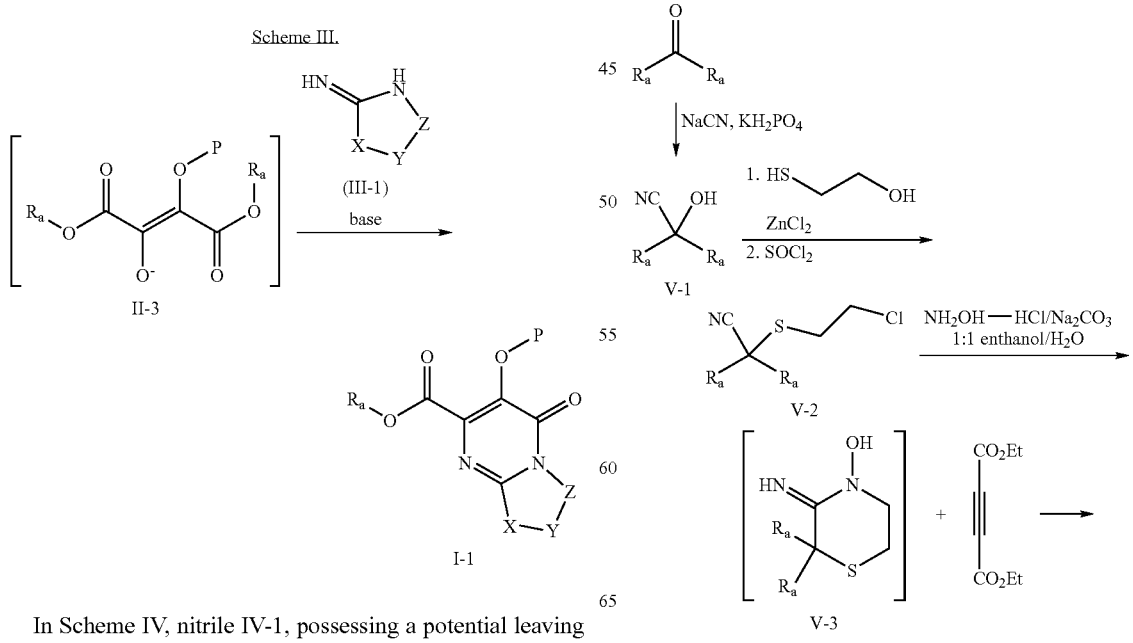

In Scheme IV, nitrile IV-1, possessing a potential leaving group B, can be reacted with hydroxylamine to form inter-

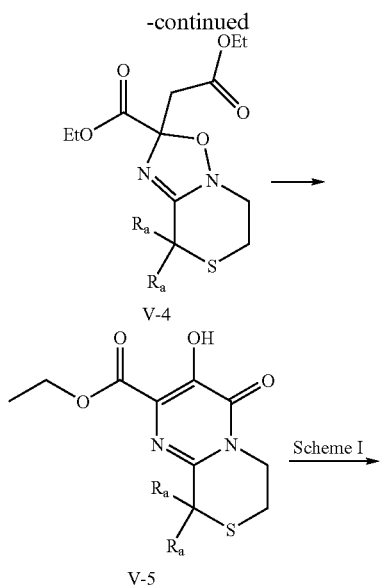
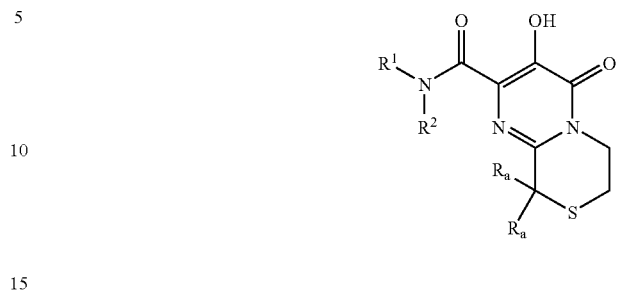
In Scheme VI, bicyclic intermediate VI-1, prepared according to the methods described above, can be saponified using well known methods. The resulting carboxylic acid, VI-3, can then be coupled to amine VI-2 using standard amide bond forming reagents and methods. Removal of the benzyl group, by hydrogenolysis or acid mediated hydrolysis provides the final products.
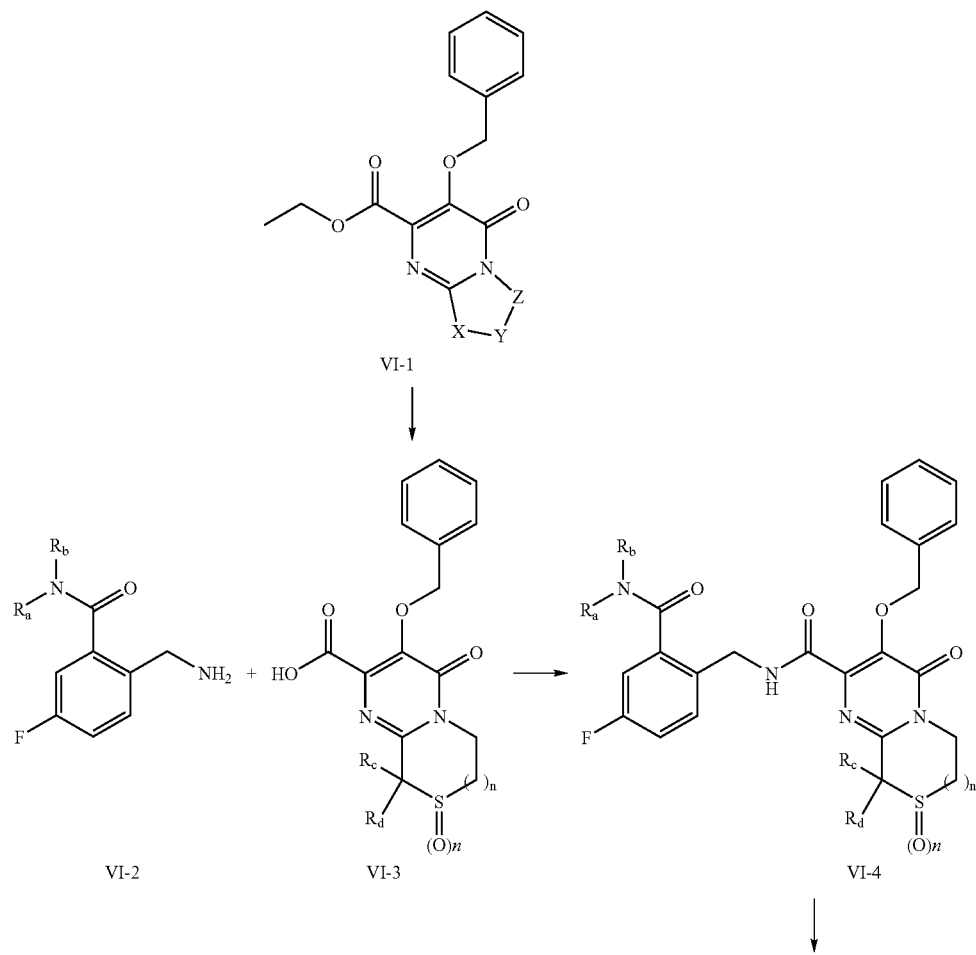

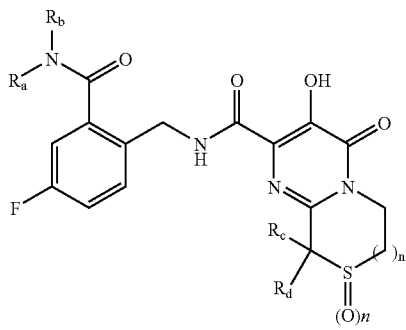

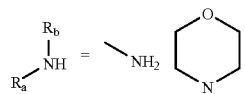

$R_c, R_d =$ —H, —CH$_3$, —CH$_2$CH$_3$, —CH(CH$_3$)$_2$
n = 1 or 2

An alternative route to compounds similar to those presented in Scheme VI is given in Scheme VII. In this scheme the ester group of VII-1 can be hydrolyzed and the resulting carboxylic acid coupled to methyl 2-(aminomethyl)-5-fluorobenzoate. A second hydrolysis reaction can produce VII-4 which can be coupled with a second amine. This is followed by removal of the benzyl group to provide the final products.

Scheme VII

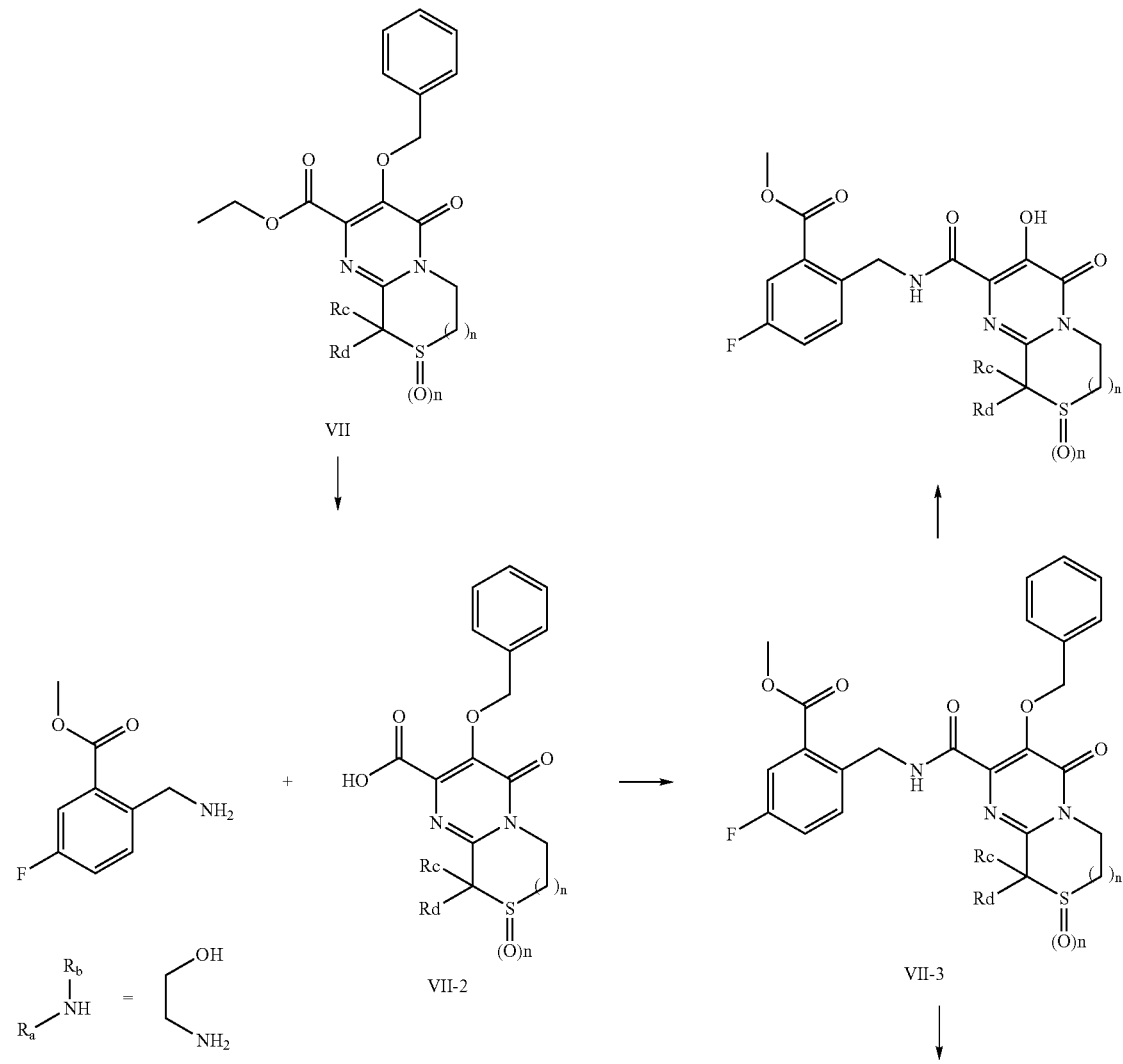

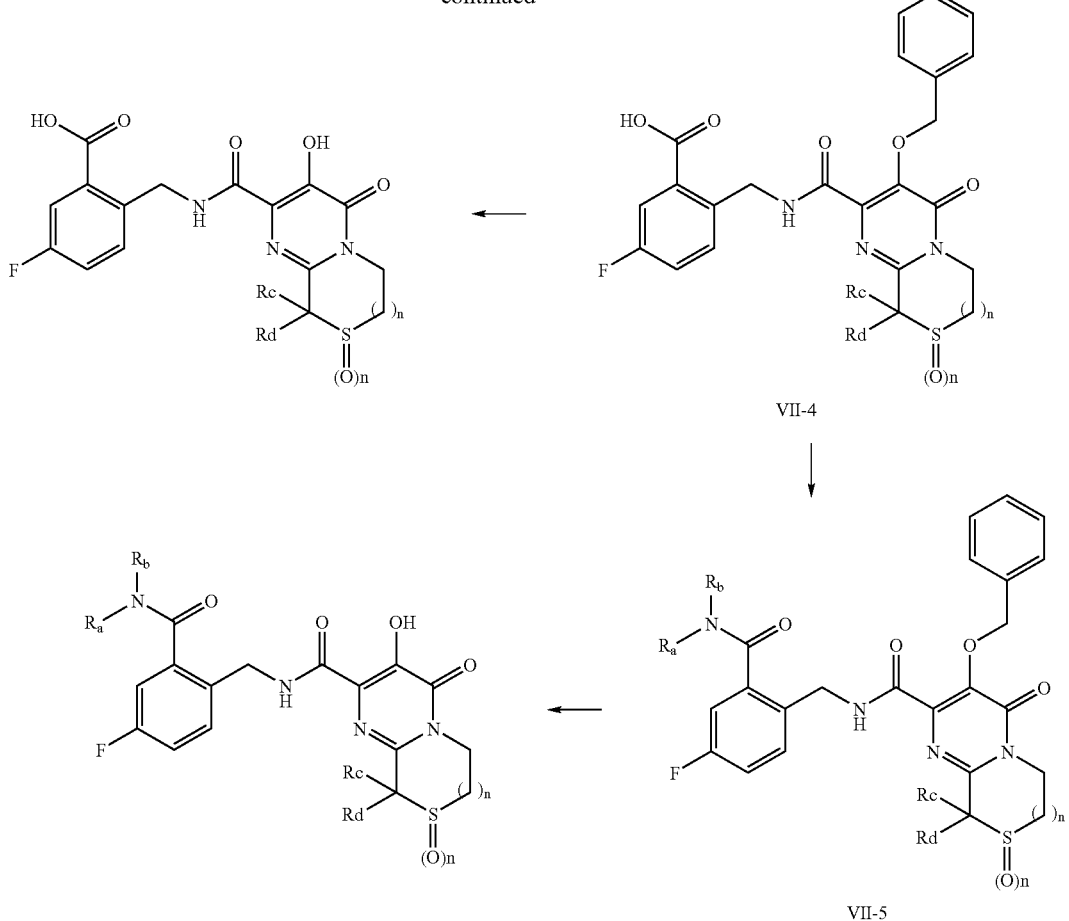
In yet another method, Scheme VIII illustrates the synthesis of sulfonamide containing examples, starting from 5-fluoro-2-methylbenzen-1-sulfonyl chloride.
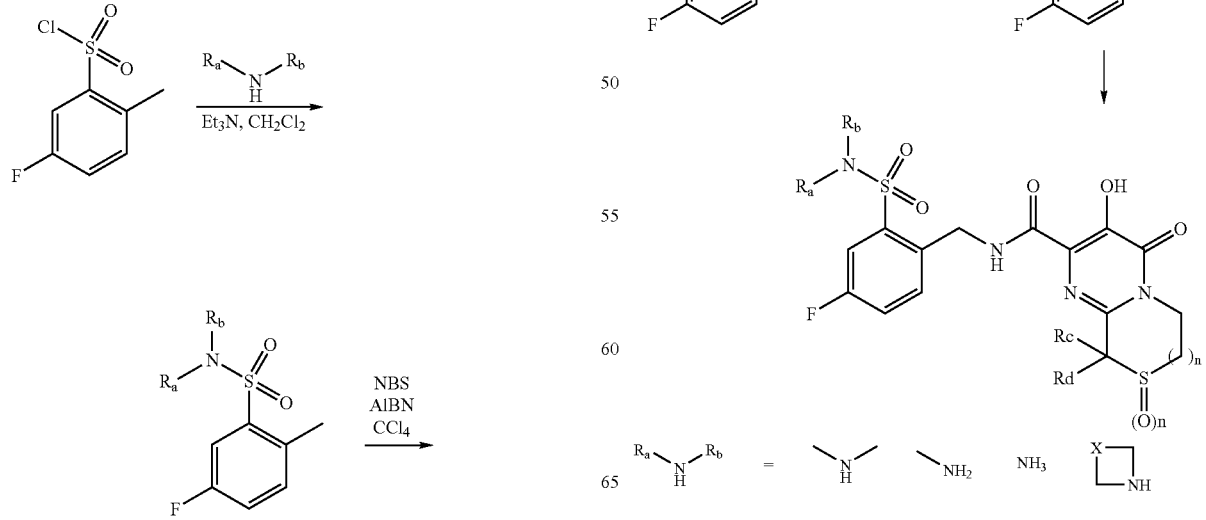

Further illustration of methods used for the synthesis of certain compounds of the invention is shown in Scheme IX. Methylation of 5-(2-bromo-5-fluorophenyl)-1H-tetrazole can yield a mixture of IX-1 and IX-2 that can be separated and each of the compounds carried on to the corresponding final products.
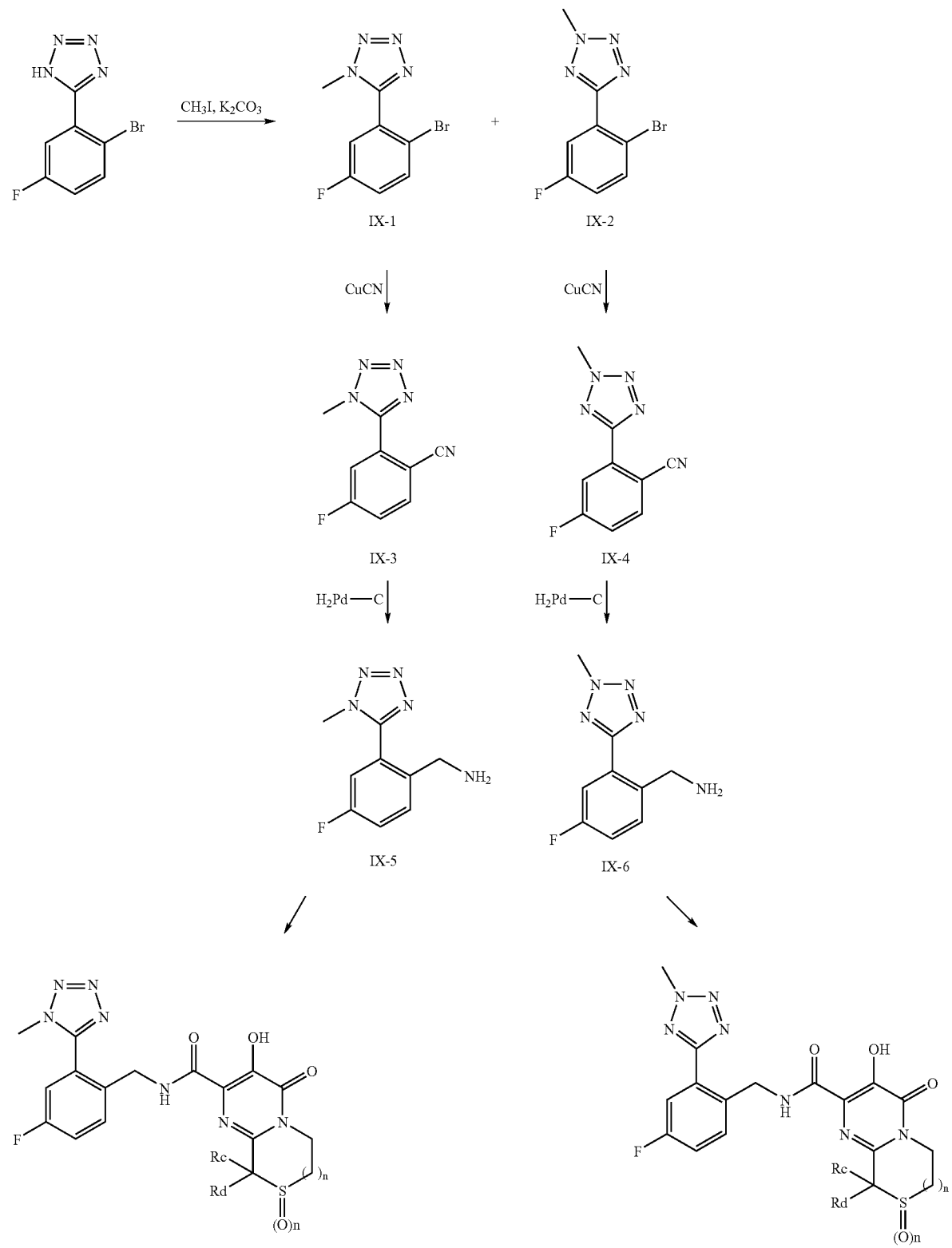
Scheme IX Some examples of the invention can be synthesized according to the methods illustrated in Schemes X-XIV.
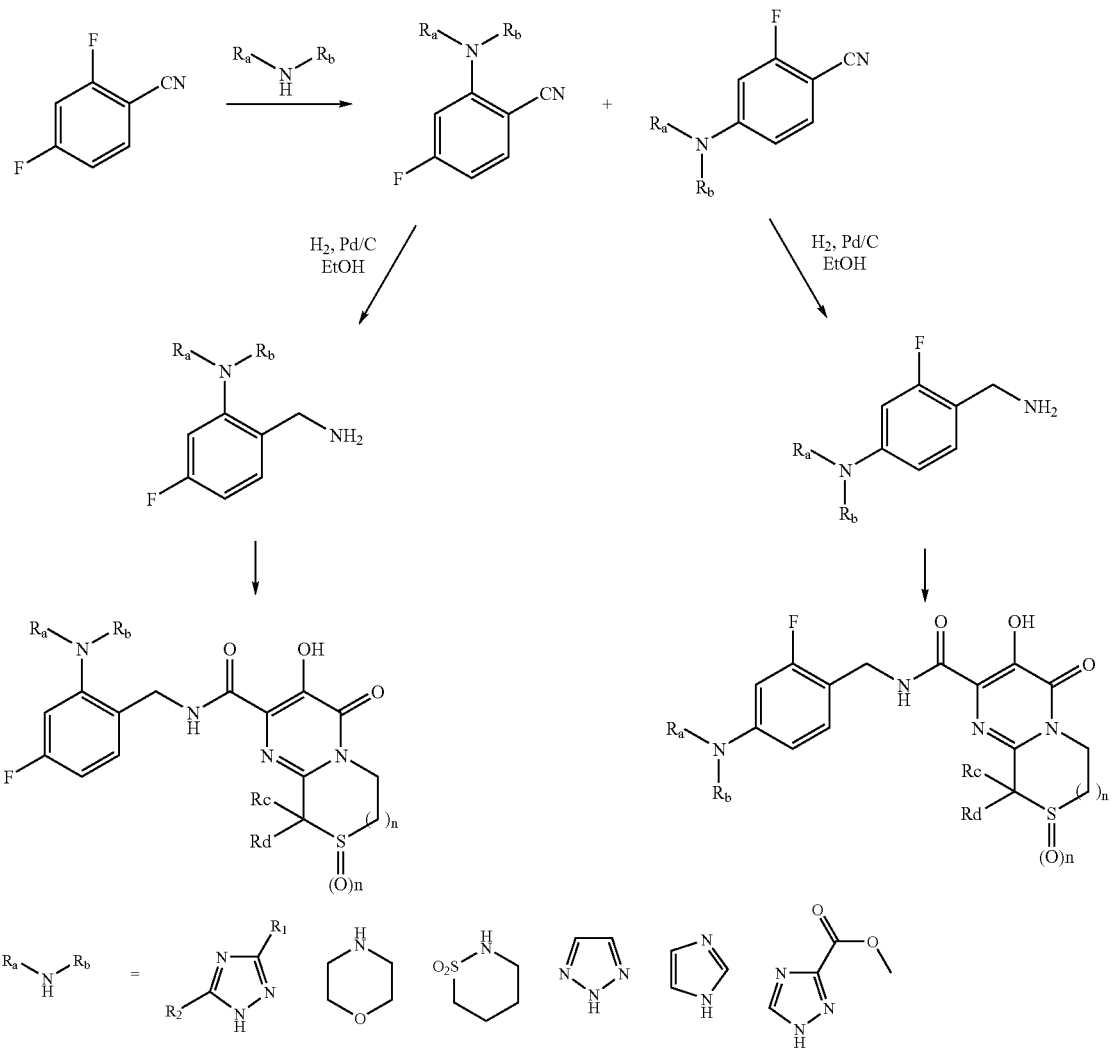
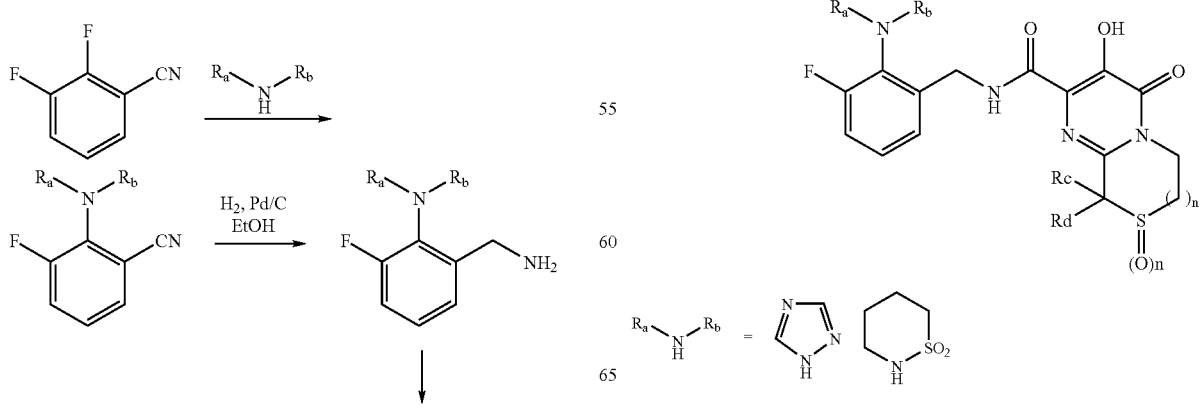

Scheme XII
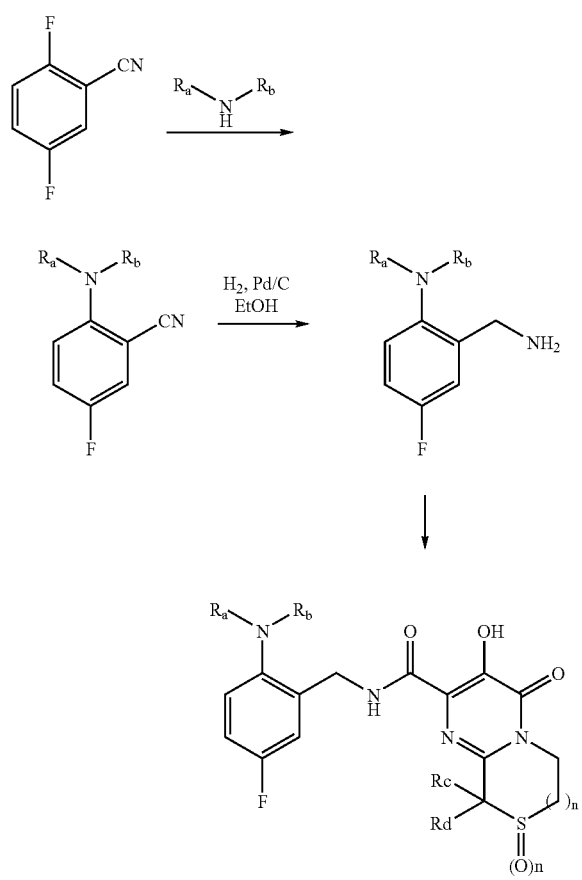
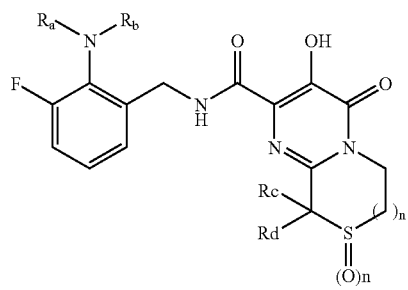
Scheme XIII
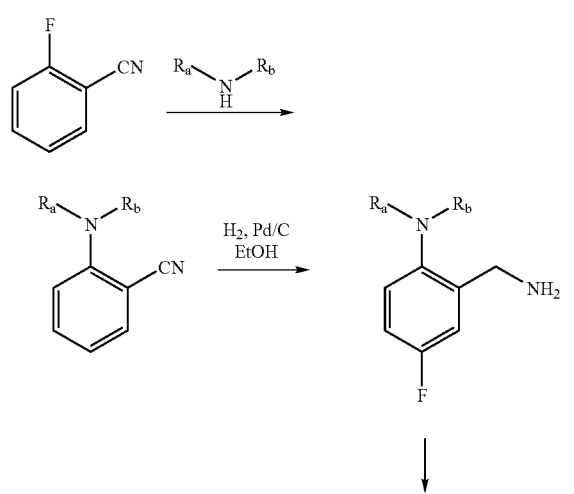
Scheme XIV
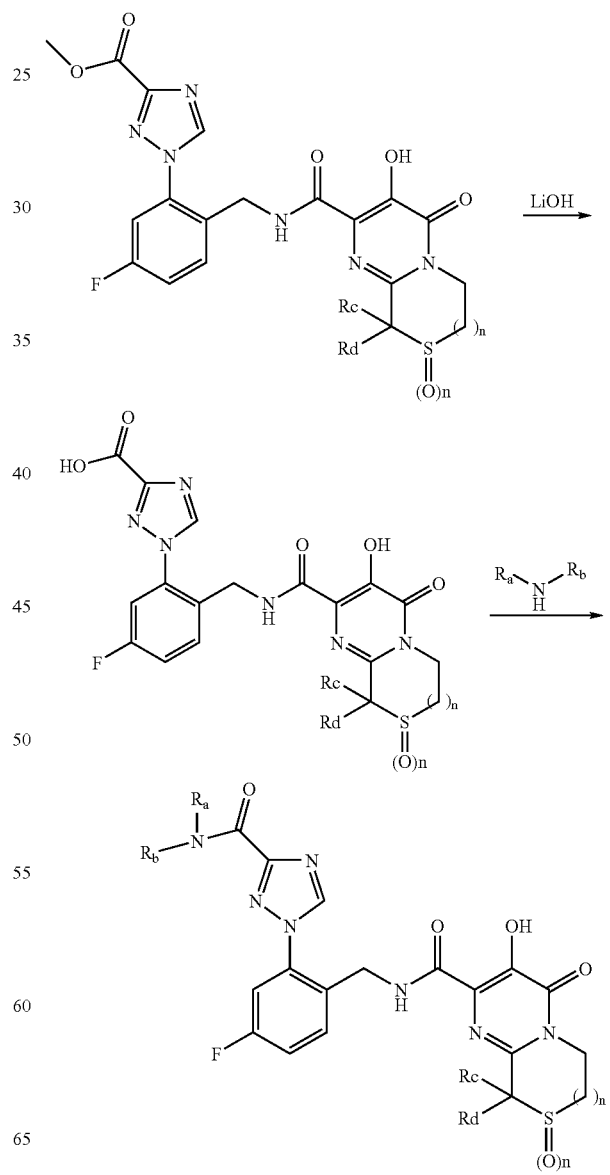

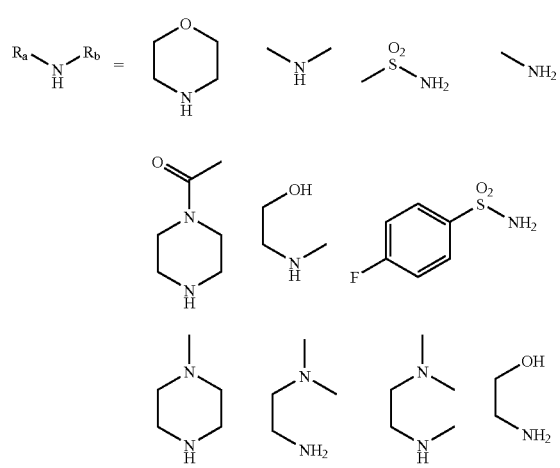
Some Formula I compounds can be made according to Schemes XV-XIX.
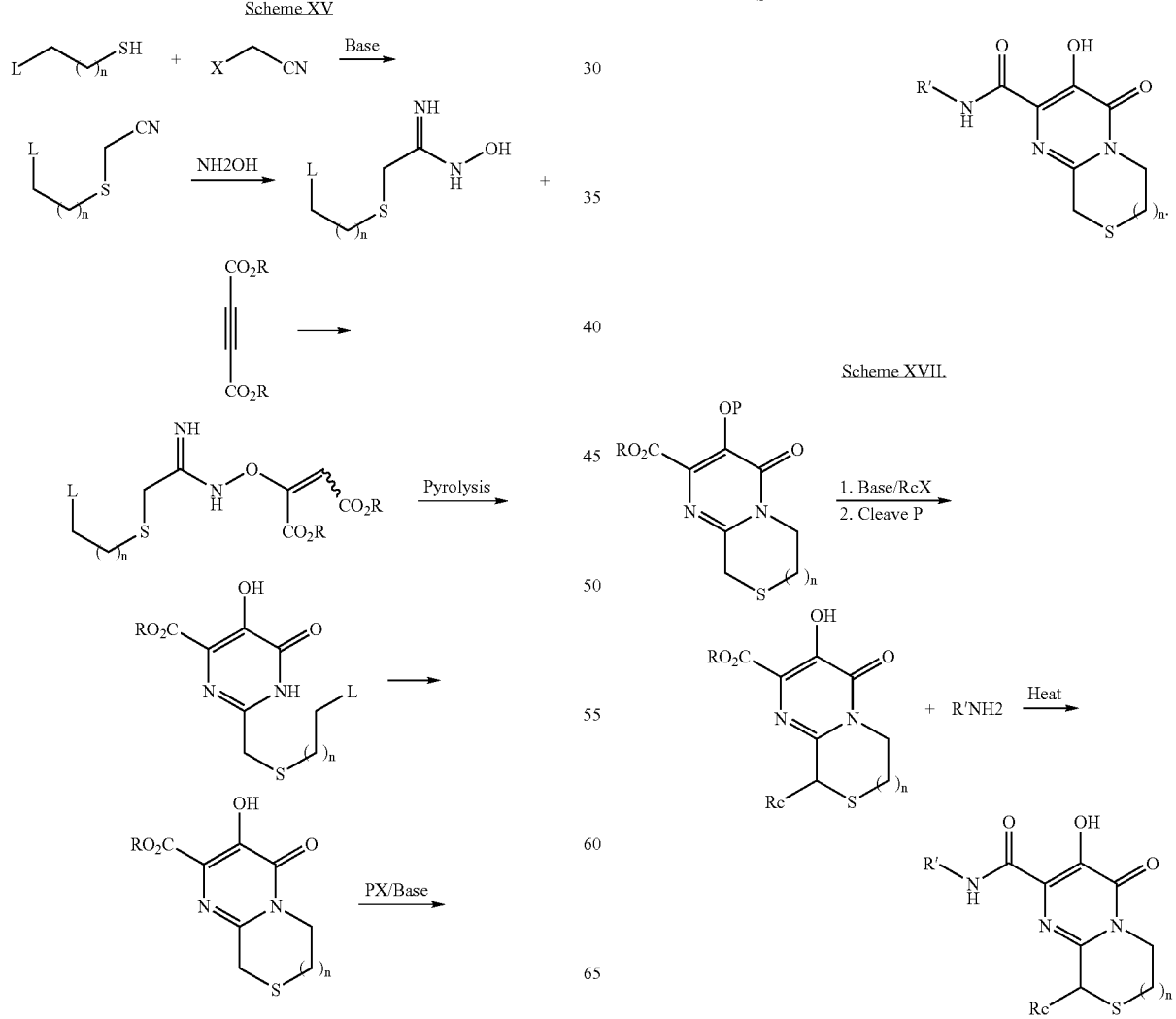
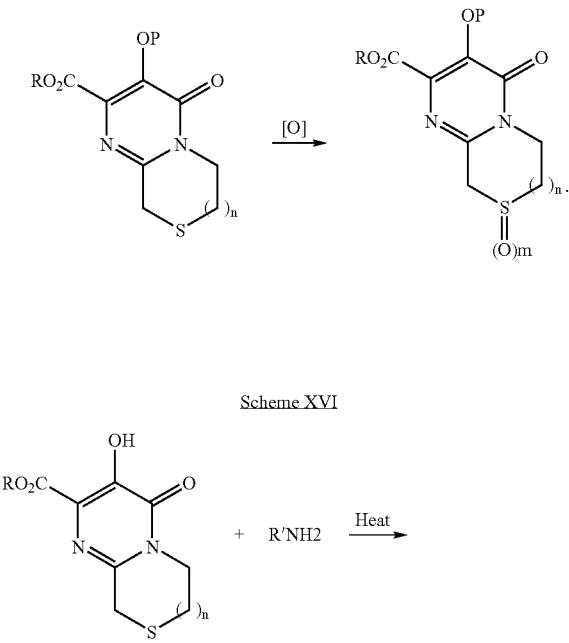

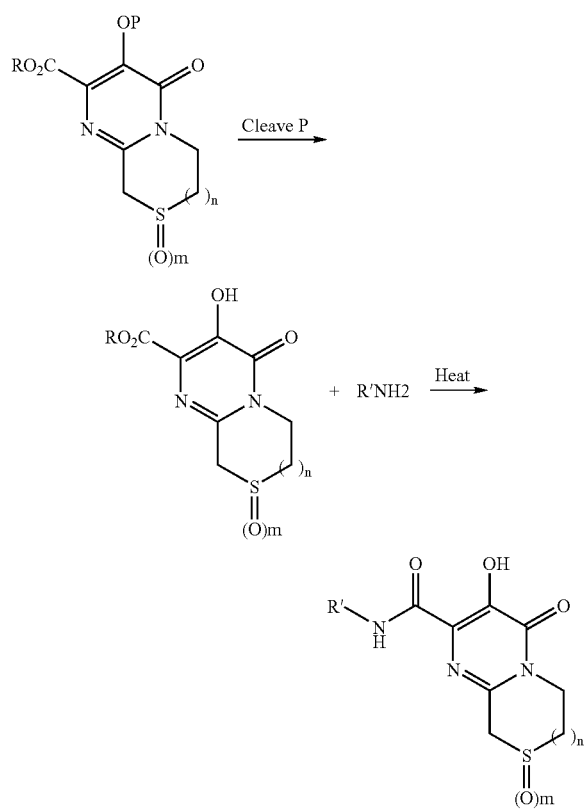

Scheme XVIII.

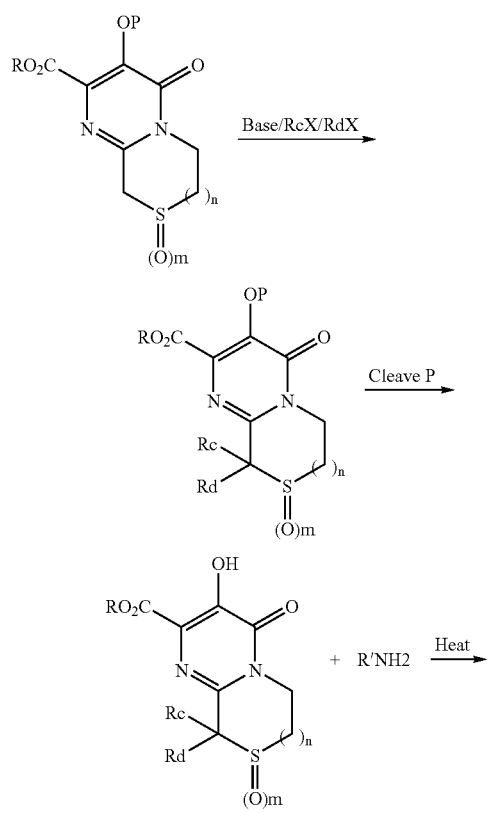

Scheme XIX.

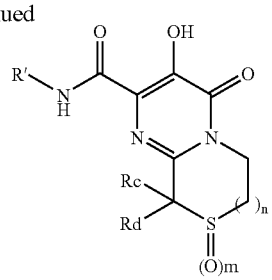

Biological Methods

HIV-Integrase Inhibition Activity. To evaluate in-vitro activity against HIV-integrase, 5 pmole of biotin labeled substrate DNA was bound to 100 µg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994). Results are shown in the Table 1. Activity equal to A refers to a compound having $IC_{50}$=0.002 to 0.10 µM while B and C denote compounds having $IC_{50}$=0.1 to 1.0 µM and $IC_{50} \geq 1.0$ µM respectively.

TABLE 1

| Example | Activity |
|---------|----------|
| 1 | A |
| 2 | B |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}=0.003$ to 0.10 μM while B and C denote compounds with $EC_{50}=0.1$ to 1.0 μM and $EC_{50} \geq 1.0$ μM respectively.

TABLE 2

| Example | Activity |
|---------|----------|
| 1 | B |
| 2 | C |
| 3 | B |
| 4 | B |
| 5 | A |
| 6 | A |
| 7 | A |
| 8 | B |
| 9 | B |
| 10 | B |
| 11 | C |
| 12 | A |
| 13 | A |
| 14 | A |
| 15 | A |
| 16 | B |
| 17 | B |
| 18 | B |
| 19 | A |
| 20 | A |
| 21 | C |
| 22 | A |
| 23 | A |
| 24 | A |
| 25 | A |
| 26 | A |
| 27 | A |
| 28 | A |
| 29 | — |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 4 lists some agents useful in treating AIDS and HIV infection which are suitable for this invention.

TABLE 4

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |

TABLE 4-continued

| DRUG NAME | MANUFACTURER | INDICATION |
|---|---|---|
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |

TABLE 4-continued

| DRUG NAME | MANUFACTURER | INDICATION |
|---|---|---|
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim Isethionate for Inhalation | Burroughs Wellcome Fisons Corporation | PCP treatment PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Intermediates 1 and 2

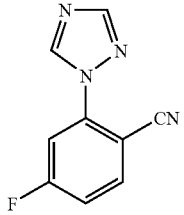

1

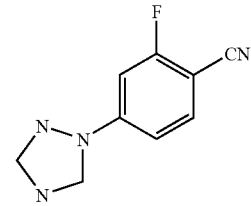

2

To a solution of 2,4-difluorobenzonitrile (10 g, 72 mmol) dissolved in THF (20 mL), and DMF (40 mL) was added 1,2,4-triazole sodium derivative (6.3 g, 70 mmol) and the mixture was stirred at 90° C. for 3 h, filtered and concentrated. The residue was adsorbed onto Silica gel and purified by flash chromatography eluting with 0%-10%-30% EtOAc/hexanes to give intermediate 1 as colorless needles (2.46 g, 18%) and intermediate 2 was obtained as a white solid (0.7455 g, 6%).

Intermediate 1

4-Fluoro-2-(1H-1,2,4-triazol-1-yl)benzonitrile: $^1$H NMR (500 MHz, CDCl$_3$) δ: 8.89 (1H, s), 8.19 (1H, s), 7.85 (1H, dd, J=8.7, 5.6 Hz), 7.60 (1H, dd, J=8.8, 2.4 Hz), 7.28-7.24 (1H, m). LCMS (M+H) calcd for C$_9$H$_6$N$_4$F: 189.05. found: 189.13.

Intermediate 2

4-(1H-1,2,4-triazol-1-yl)-2-fluorobenzonitrile: $^1$H NMR (500 MHz, CDCl$_3$) δ: 8.66 (1H, s), 8.15 (1H, s), 7.79 (1H, dd, J=8.5, 6.7 Hz), 7.69 (1H, dd, J=9.5, 1.8 Hz), 7.65-7.63 (1H, m). LCMS (M+H) calcd for C$_9$H$_6$N$_4$F: 189.05. found: 189.13.

Intermediate 3

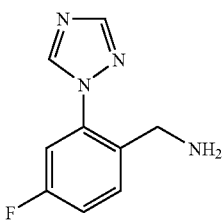

(4-Fluoro-2-(1H-1,2,4-triazol-1-yl)phenyl)methanamine hydrochloride: Intermediate 1 (2.46 g, 13.13 mmol) was dissolved in hot ethanol (150 mL). Aqueous HCl (15 mL, 1N) was added followed by 10% Pd/C (200 mg). The mixture was shaken under H$_2$ at 55 psi for 4 h., filtered over celite and concentrated. The residue was partitioned between EtOAc and water. The aqueous phase was lyophilized to give intermediate 3 as a white powder (2.96 g, 99%). $^1$H NMR (500 MHz, CD$_3$OD) δ: 9.51 (1H, s), 8.63 (1H, s), 7.85 (1H, dd, J=8.5, 5.8 Hz), 7.68 (1H, dd, J=8.8, 2.4 Hz), 7.49 (1H, td, J=8.3, 2.4 Hz), 4.20 (2H, s). LCMS (M+H) calcd for C$_9$H$_{10}$N$_4$F: 193.08. found: 193.16.

Intermediate 4

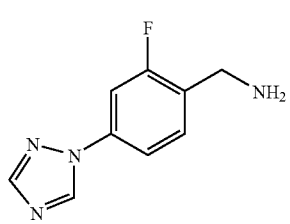

(4-Fluoro-2-(1H-1,2,4-triazol-1-yl)phenyl)methanamine hydrochloride: Intermediate 4 was prepared (79% yield) following the procedure for intermediate 3 using intermediate 2. $^1$H NMR (500 MHz, CD$_3$OD) δ: 9.25 (1H, s), 8.46 (1H, s), 7.80 (1H, dd, J=8.6, 5.8 Hz), 7.64 (1H, dd, J=8.8, 2.4 Hz), 7.44 (1H, td, J=8.3, 2.6 Hz), 4.17 (2H, s). LCMS (M+H) calcd for C$_9$H$_{10}$N$_4$F: 193.08. found: 193.16.

Intermediate 5 and 6

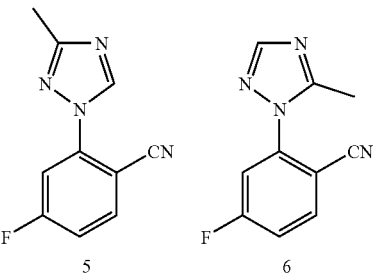

A solution of 2,4-difluorobenzonitrile (7.07 g, 50.8 mmol) and 3-methyl-1H-1,2,4-triazole (4.22 g, 50.8 mmol) in N,N-dimethylformamide (45 ml) was treated with powdered anhydrous potassium carbonate (10 g) and the resulting mixture was stirred at 22° C. for 18 h. The solid was then filtered and the filtrate was concentrated in vacuo. The residue was diluted with ethyl acetate, washed with water and brine, dried over anhydrous magnesium sulfate and concentrated. The mixture containing the 2 and 4-triazolyl-benzonitriles was purified by a combination of chromatography on silica gel (elution gradient of ethyl acetate in hexane) and on reversed phase silica gel to give 1.86 g (18% yield) of Intermediate 5 and 0.526 g (5% yield) of Intermediate 6.

Intermediate 5

4-Fluoro-2-(3-methyl-1H-1,2,4-triazol-1-yl)benzonitrile: White crystals (ethyl acetate/hexanes); mp 117-118° C. $^1$H NMR (400 MHz, CDCl$_3$) δ: 8.82 (1H, s), 7.84 (1H, dd, J=5.6, 8.6 Hz), 7.62 (1H, dd, J=2.5, 9.1 Hz), 7.24 (1H, m), 2.54 (3H, s). Anal. Calcd for C$_{10}$H$_7$FN$_4$: C, 59.40; H, 3.49; N, 27.71. found: C, 59.25; H, 3.32; N, 27.81.

Intermediate 6

4-fluoro-2-(5-methyl-1H-1,2,4-triazol-1-yl)benzonitrile: White crystals (ethyl acetate-hexane); mp 120-121° C. $^1$H NMR (400 MHz, CDCl$_3$) δ: 8.06 (1H, s), 7.91 (1H, dd, J=5.5, 8.6 Hz), 7.39 (1H, m), 7.30 (1H, dd, J=2.5, 8.1 Hz), 2.56 (3H, s). Anal. Calcd for C$_{10}$H$_7$FN$_4$: C, 59.4; H, 3.49; N, 27.71. found: C, 59.35; H, 3.70; N, 27.77.

Intermediate 7

(4-Fluoro-2-(3-methyl-1H-1,2,4-triazol-1-yl)phenyl) methanamine hydrochloride salt. Hydrogenation of intermediate 5 (0.680 g, 3.36 mmol) gave 0.720 g (88% yield) of the title hydrochloride salt as a white solid. $^1$H NMR (400 MHz, DMSO-d$_6$) δ: 9.00 (1H, s), 7.84 (1H, dd, J=6.1, 9.1 Hz), 7.62

(1H, dd, J=2.8, 9.3 Hz), 7.50 (1H, m), 4.02 (2H, m), 2.40 (3H, s). HRMS calcd for $C_{10}H_{12}FN_4$ [M+H]: 207.1046. found: 207.1047.

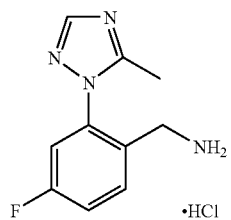

Intermediate 8

(4-Fluoro-2-(5-methyl-1H-1,2,4-triazol-1-yl)phenyl) methanamine hydrochloride salt. Hydrogenation of intermediate 6 (0.244 g, 1.20 mmol) gave 0.290 g (100% yield) of the title hydrochloride salt as a white solid. $^1$H NMR (400 MHz, DMSO-$d_6$) δ: 8.22 (1H, s), 7.90 (1H, dd, J=6.0, 8.6 Hz), 7.67 (1H, dd, J=2.8, 9.3 Hz), 7.58 (1H, m), 3.78 (2H, m), 2.42 (3H, s). HRMS calcd for $C_{10}H_{12}FN_4$ [M+H]: 207.1046. found: 207.1041.

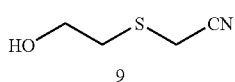

Intermediate 9

2-(2-hydroxyethylthio)acetonitrile: To a stirred solution of 2-mercaptoethanol (17.53 mL, 250 mmol) in THF (120 mL) was added $K_2CO_3$ (41.5 g, 300 mmol) followed by chloroacetonitrile (17.0 mL, 270 mmol). After 48 h at room temperature, the reaction mixture was diluted with $CH_2Cl_2$ (200 mL), filtered through a plug of celite and concentrated to give dark red oil (26.67 g, 91%) which was used in the subsequent step without purification. $^1$H NMR (500 MHz, CDCl$_3$) δ: 3.91 (2H, t, J=5.5 Hz), 3.40 (2H, s), 2.94 (2H, t, J=5.5 Hz), 2.00 (1H, br s).

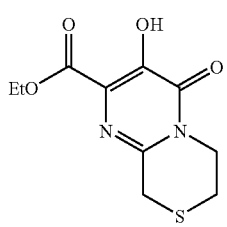

Intermediate 10

Ethyl 3-hydroxy-4-oxo-4,6,7,9-tetrahydropyrimido[2,1-c][1,4]thiazine-2-carboxylate: A mixture of intermediate 9 (14.79 g, 126 mmol) and 50% aqueous hydroxylamine (7.65 mL, 125 mmol) in ethanol (100 mL) was heated at 80° C. for 2 h. Then, cooled in an ice-water bath and diethyl acetylenedicarboxylate (20 mL, 125 mmol) was added over 10 minutes. After 2 h at room temperature, the reaction mixture was concentrated and the resulting dark residue was taken up in EtOAc (200 mL), washed successively with water (50 mL) and brine (50 mL), and dried (Na$_2$SO$_4$), filtered and concentrated to afford yellow oil which was used in the next step.

A solution of above yellow oil in xylenes (200 mL) was heated at reflux for 15 h. Then, the reaction mixture was cooled and extracted with 0.5 M aq. Na$_2$CO$_3$ (3×40 mL). The combined extracts were washed with EtOAc (50 mL), acidified with conc. HCl and extracted with CH$_2$Cl$_2$ (4×50 mL). The combined CH$_2$Cl$_2$ extracts dried (Na$_2$SO$_4$), filtered and concentrated to give dark solid (6.81 g).

To a stirred solution of above dark solid (6.81 g, ~24.8 mmol) and methanesulfonyl chloride (5.8 mL, 75 mmol) in THF (200 mL) at 0° C. was added Et$_3$N (11 mL, 78.6 mmol) over 5 minutes. The reaction mixture was stirred for 4 h while allowing it to warm to ambient temperature. After 1 h at room temperature, the reaction mixture was diluted with EtOAc (200 mL), washed with water (2×50 mL) and brine (50 mL). The organic layer dried (Na$_2$SO$_4$), filtered and concentrated to afford dark paste.

The above dark paste (7.6 g) was dissolved in 2:1 THF/EtOH (150 mL) and treated with K$_2$CO$_3$ (2.07 g, 15 mmol). After stirring for 48 h at room temperature, the reaction mixture was concentrated, and the residue was taken up in water (100 mL), neutralized with conc. HCl and extracted with CH$_2$Cl$_2$ (5×50 mL). The combined CH$_2$Cl$_2$ dried (Na$_2$SO$_4$), filtered and concentrated to give dark brown paste which was stirred with EtONa (15 mmol) in EtOH for 5 h at room temperature. Then, the reaction mixture was concentrated and the resulting residue was taken up in water (100 mL), and extracted with EtOAc (3×50 mL). The organic extracts were discarded and aq. layer acidified with conc. HCl and extracted with CH$_2$Cl$_2$ (5×50 mL). The combined CH$_2$Cl$_2$ extracts were dried (Na$_2$SO$_4$), filtered and concentrated to give dark paste (1.3866 g, 4.3%, 80% pure) which was used in the next step without further purification. LRMS (M+H) calcd for 257.06. found: 257.12.

Example 1

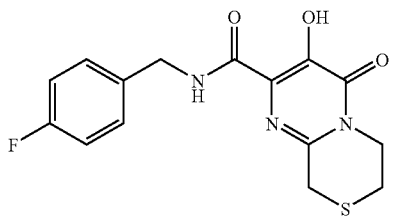

N-(4-fluorobenzyl)-3-hydroxy-4-oxo-4,6,7,9-tetrahydropyrimido[2,1-c][1,4]thiazine-2-carboxamide: A solution of intermediate 10 (0.213 g, 0.831 mmol), 4-fluorobenzylamine (0.23 mL, 2 mmol) and Et$_3$N (0.28 mL, 2 mmol) in DMF/EtOH (1:1, 5 mL) was heated at 110° C. in a sealed vial for 2 h. Then, the reaction mixture was cooled and purified by Prep-HPLC to afford product as white solid (0.076 g, 27%). $^1$H NMR (500 MHz, CDCl$_3$) δ: 12.14 (1H, s), 7.87 (1H, br s), 7.32-7.29 (2H, m), 7.04 (2H, t, J=8.7 Hz), 4.57 (2H, d, J=6.1 Hz), 4.42 (2H, t, J=6.1 Hz), 3.65 (2H, s), 3.04 (2H, t, J=6.1

Hz). HRMS (M+H) calcd for $C_{15}H_{15}FN_3O_3S$: 336.0818. found: 336.0811. Anal calcd for $C_{15}H_{14}FN_3O_3S$: C, 53.72; H, 4.20; N, 12.53. found: C, 53.52; H, 4.10; N, 12.37.

Intermediate 11

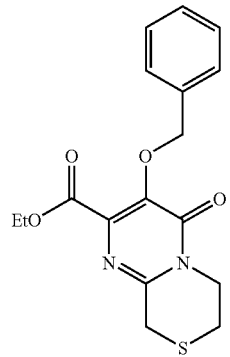

11

Ethyl 3-(benzyloxy)-4-oxo-4,6,7,9-tetrahydropyrimido[2,1-c][1,4]thiazine-2-carboxylate: A mixture of intermediate 9 (16.6 g, 141.675 mmol) and 50% aqueous hydroxylamine (18.4 mL, 300 mmol) in ethanol (100 mL) was stirred room temperature for 48 h and heated at 50° C. for 1 h. Then, the reaction mixture was concentrated to remove EtOH and the residue was freeze dried to afford white powder. This was dissolved in EtOH/H$_2$O (1:2, 200 mL), cooled in an ice-water bath and diethyl acetylenedicarboxylate (20 mL, 125 mmol) was added over 10 minutes. After 2 h at room temperature, the reaction mixture concentrated and the resulting turbid residue was taken up in EtOAc (200 mL), washed successively with water (2×75 mL) and brine (50 mL), and dried (Na$_2$SO$_4$), filtered and concentrated to afford yellow oil.

A solution of above yellow oil in xylenes (1.0 Lit.) was heated at reflux for 6 h. Then, the reaction dark mixture was cooled and concentrated to give dark solid. This solid was dissolved into 0.33 N aq. NaOH (450 mL), filtered and freeze dried to give black powder.

To a stirred slurry of above black powder in DMF (250 mL) was added methanesulfonylchloride (15.4 mL, 200 mmol), cooled in an ice-water bath and treated with Et$_3$N (28 mL, 200 mmol). After 4 h at room temperature, DMF was removed under vacuo and the resulting residue was triturated with THF (250 mL), filtered and concentrated to afford black paste.

A mixture of above black paste and K$_2$CO$_3$ (13.8 g, 100 mmol) in DMF/EtOH (1:1, 200 mL) was stirred at 70° C. for 4 h. To this was carefully added benzyl bromide (8.92 mL, 75 mmol) and K$_2$CO$_3$ (7 g, 50 mmol) and stirred additional 16 h at 70° C. Then, the reaction mixture was concentrated and the resulting residue was taken up in EtOAc (250 mL), washed with water (3×50 mL), brine (50 mL), dried (Na$_2$SO$_4$), filtered and concentrated to give dark paste. Flash chromatography on silica gel column using mixtures of 30-60% EtOAc/Hex provided title compound as an orange paste. Crystallization from Et$_2$O/Hex gave product as a white solid (2.8764 g, 5.86%). $^1$H NMR (500 MHz, CDCl$_3$) δ: 7.48-7.46 (2H, m), 7.37-7.30 (3H, m), 5.27 (2H, s), 4.40 (2H, t, J=5.5 Hz), 4.35 (2H, q, J=7.0 Hz), 3.77 (2H, s), 3.07 (2H, t, J=6.1 Hz), 1.31 (3H, t, J=7.0 Hz). HRMS (M+H) calcd for $C_{17}H_{19}N_2O_4S$: 347.1066. found: 347.1080.

Intermediate 12

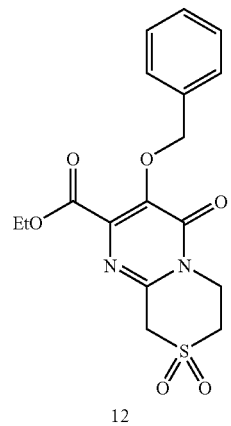

12

Pyrimido[2,1-c][1,4]thiazine-2-carboxylic acid, 4,6,7,9-tetrahydro-4-oxo-3-(phenylmethoxy)-, ethyl ester, 8,8-dioxide: To a stirred solution of intermediate 11 (2.764 g, 7.9792 mmol) in CH$_2$Cl$_2$ (100 mL) was added mCPBA (57-86%, 4.266 g, 17.55 mmol) over 5 min and stirred at room temperature for 1.5 h. Then, saturated aq. NaHCO$_3$ (20 mL) and aq. 10% Na$_2$S$_2$O$_3$ solution (10 mL) were added and stirred for additional 20 min. Then, the reaction mixture was transferred to separatory funnel and aq. layer discarded. The organic layer washed with saturated aq. NaHCO$_3$ (20 mL), brine (20 mL), dried (Na$_2$SO$_4$), filtered and concentrated to give yellow residue which was triturated with ether/CH$_2$Cl$_2$ and filtered to provide product as white solid (2.6933 g, 89%). $^1$H NMR (500 MHz, CDCl$_3$) δ: 7.46-7.44 (2H, m), 7.38-7.32 (3H, m), 5.31 (2H, s), 4.72 (2H, t, J=5.9 Hz), 4.47 (2H, s), 4.34 (2H, q, J=7.0 Hz), 3.49 (2H, t, J=6.1 Hz), 1.31 (3H, t, J=7.0 Hz). HRMS (M+H) calcd for $C_{17}H_{19}N_2O_6S$: 379.0964. found: 379.0974.

Example 2

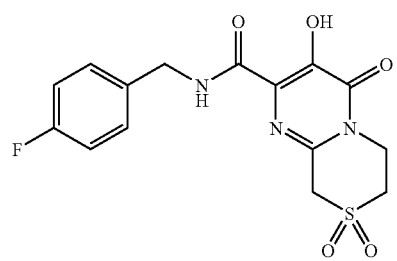

Pyrimido[2,1-c][1,4]thiazine-2-carboxamide, N-[(4-fluorophenyl)methyl]-4,6,7,9-tetrahydro-3-hydroxy-4-oxo-, 8,8-dioxide: A solution of intermediate 12 (0.0567 g, 0.15 mmol) in trifluoroacetic acid (3 mL) was stirred for 1.5 h at room temperature and then concentrated to give white solid. The solid was added 4-fluorobenzyl amine (0.125 g, 1 mmol), Et$_3$N (0.14 mL, 1 mmol), EtOH (5 mL) and stirred at 90° C. for 24 h. Then, the reaction mixture was cooled and purified preparative HPLC using MeOH/H$_2$O as eluent to afford product as white solid (0.0463 g, 84%). $^1$H NMR (500 MHz, CDCl$_3$) δ: 12.52 (1H, s), 7.74 (1H, br s), 7.33-7.30 (2H, m), 7.06 (2H, t, J=8.7 Hz), 4.75 (2H, t, J=6.0 Hz), 4.57 (2H, d, J=6.1 Hz), 4.37 (2H, s), 3.49 (2H, t, J=6.0 Hz). HRMS (M+H) calcd for $C_{15}H_{15}FN_3O_5S$: 368.0716. found: 378.0704. Anal calcd for $C_{15}H_{14}FN_3O_5S$: C, 49.04; H, 3.84; N, 11.43. found: C, 49.17; H, 3.59; N, 11.20.

Intermediate 13 and 14

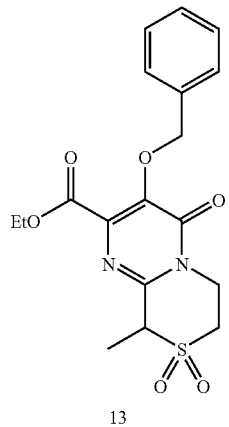

13

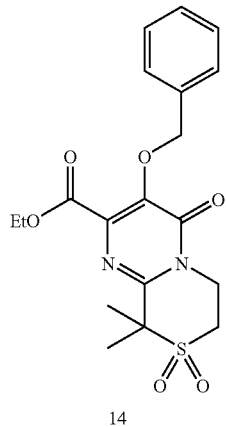

14

To a stirred yellow mixture of intermediate 12 (0.3784 g, 1 mmol) and $Cs_2CO_3$ (0.6516 g, 2 mmol) in DMF (10 mL) at room temperature was added methyl iodide (0.16 mL, 2.5 mmol). After 6 h, the reaction mixture was diluted with $Et_2O$ (50 mL), washed with 1N aq. HCl (10 mL), water (2×10 mL), brine (10 mL), dried ($Na_2SO_4$), filtered and concentrated to give yellow residue. Flash chromatographic purification on silica gel column using 3:7 EtOAc/Hex followed by 2:3 EtOAc/Hex provided intermediates 13 and 14.

Intermediate 13

Pyrimido[2,1-c][1,4]thiazine-2-carboxylic acid, 4,6,7,9-tetrahydro-9-methyl-4-oxo-3-(phenylmethoxy)-, ethyl ester, 8,8-dioxide: White solid (0.2765 g, 68%). $^1$H NMR (500 MHz, $CDCl_3$) δ: 7.46 (2H, d, J=8.6 Hz), 7.38-7.31 (3H, m), 5.27 (2H, s), 4.60 (2H, t, J=6.4 Hz), 4.33 (2H, q, J=7.0 Hz), 3.53 (2H, t, J=6.4 Hz), 1.82 (6H, s), 1.30 (3H, t, J=7.0 Hz). HRMS (M+H) calcd for $C_{18}H_{21}N_2O_6S$: 393.1120. found: 393.1129.

Intermediate 14

Pyrimido[2,1-c][1,4]thiazine-2-carboxylic acid, 4,6,7,9-tetrahydro-9,9-dimethyl-4-oxo-3-(phenylmethoxy)-, ethyl ester, 8,8-dioxide: White solid (0.086 g, 22%). $^1$H NMR (500 MHz, $CDCl_3$) δ: 7.45 (2H, d, J=7.3 Hz), 7.38-7.33 (3H, m), 5.47-5.42 (1H, m), 5.34 (1H, d, $J_{AB}$=11.0 Hz), 5.25 (1H, d, $J_{AB}$=11.0 Hz), 4.36-4.31 (3H, m), 4.12-4.05 (1H, m), 3.65 (1H, dt, J=14.0, 3.7 Hz), 3.39-3.33 (1H, m), 1.81 (3H, d, J=6.7 Hz), 1.30 (3H, t, J=7.0 Hz). HRMS (M+H) calcd for $C_{19}H_{23}N_2O_6S$: 407.1277. found: 407.1277.

Example 3

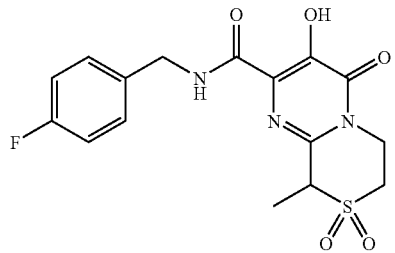

Pyrimido[2,1-c][1,4]thiazine-2-carboxamide, N-[(4-fluorophenyl)methyl]-4,6,7,9-tetrahydro-3-hydroxy-9-methyl-4-oxo-, 8,8-dioxide: A solution of intermediate 13 (0.042 g, 0.107 mmol) in trifluoroacetic acid (3 mL) was stirred for 1 h at room temperature and then concentrated. The resulting residue was dissolved in EtOH:DMF (1:1, 3 mL). To this solution was added 4-fluorobenzyl amine (0.125 g, 1 mmol) and $Et_3N$ (0.14 mL, 1 mmol) and stirred at 90° C. for 4 h. Then, the reaction mixture was cooled and purified preparative HPLC using $MeOH/H_2O$ as eluent to afford product as white solid (0.0375 g, 92%). $^1$H NMR (500 MHz, $CDCl_3$) δ: 12.51 (1H, s), 7.72 (1H, br s), 7.32-7.29 (2H, m), 7.06 (2H, t, J=8.6 Hz), 5.58-5.53 (1H, m), 4.60 (2H, d, J=6.4 Hz), 4.33 (1H, q, J=6.7 Hz), 4.08-4.01 (1H, m), 3.67 (1H, dt, J=14.0, 3.2 Hz), 3.38-3.31 (1H, m), 1.75 (3H, d, J=6.7 Hz). HRMS (M+H) calcd for $C_{16}H_{17}FN_3O_5S$: 382.0873. found: 382.0889. Anal calcd for $C_{16}H_{16}FN_3O_5S \cdot 0.5H_2O$: C, 49.23; H, 4.39; N, 10.76. found: C, 49.37; H, 4.11; N, 10.57.

Intermediate 15

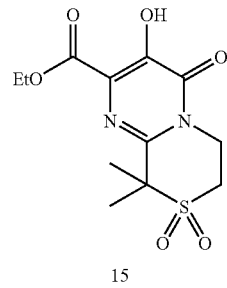

15

Pyrimido[2,1-c][1,4]thiazine-2-carboxylic acid, 4,6,7,9-tetrahydro-3-hydroxy-9,9-dimethyl-4-oxo-, ethyl ester, 8,8-dioxide: A solution of intermediate 14 (0.2315 g, 0.5696 mmol) in trifluoroacetic acid (5 mL) was stirred for 1.5 h at room temperature and then concentrated to give white solid which was crystallized from $Hex/CH_2Cl_2$ to afford product as white needles (0.1676 g, 93%). $^1$H NMR (500 MHz, $CDCl_3$) δ: 10.76 (1H, s), 4.64 (2H, t, J=6.4 Hz), 4.47 (2H, q, J=7.0 Hz), 3.55 (2H, t, J=6.4 Hz), 1.82 (6H, s), 1.44 (3H, t, J=7.0 Hz). HRMS (M+H) calcd for $C_{12}H_{17}N_2O_6S$: 317.0807. found: 317.0814.

Example 4

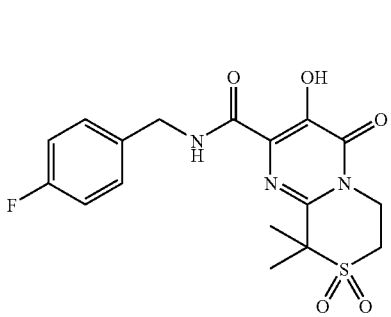

Pyrimido[2,1-c][1,4]thiazine-2-carboxamide, N-[(4-fluorophenyl)methyl]-4,6,7,9-tetrahydro-3-hydroxy-9,9-dimethyl-4-oxo-, 8,8-dioxide: A solution of intermediate 15, 4-fluorobenzylamine (0.125 g, 1 mmol) and Et$_3$N (0.14 mL, 1 mmol) in EtOH (3 mL) was heated at 90° C. for 7 h. Then, reaction mixture was cooled and purified by preparative HPLC using MeOH/H$_2$O (containing 0.1% TFA) to afford product as white solid (0.035 g, 70%). $^1$H NMR (500 MHz, CDCl$_3$) δ: 12.27 (1H, s), 7.62 (1H, br t, J=6.1 Hz), 7.31 (2H, dd, J=8.6, 5.2 Hz), 7.06 (2H, t, J=8.6 Hz), 4.66 (2H, t, J=6.4 Hz), 4.60 (2H, d, J=6.1 Hz), 3.54 (2H, t, J=6.4 Hz), 1.78 (6H, s). HRMS (M+H) calcd for C$_{17}$H$_{19}$FN$_3$O$_5$S: 396.1029. found: 396.1031. Anal calcd for C$_{17}$H$_{18}$FN$_3$O$_5$S: C, 51.64; H, 4.59; N, 10.63. found: C, 51.91; H, 4.31; N, 10.53.

Example 5-7 were prepared according to the procedure for Example 4 using intermediate 15 and appropriate amine.

Example 5

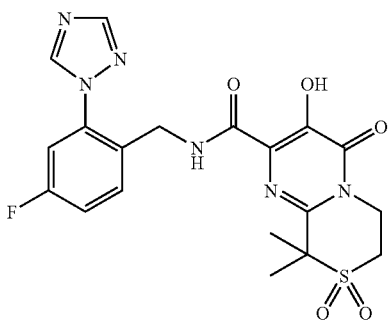

Pyrimido[2,1-c][1,4]thiazine-2-carboxamide, N-[[4-fluoro-2-(1H-1,2,4-triazol-1-yl)phenyl]methyl]-4,6,7,9-tetrahydro-3-hydroxy-9,9-dimethyl-4-oxo-, 8,8-dioxide: White solid (0.0422 g, 72%). $^1$H NMR (500 MHz, CDCl$_3$) δ: 12.25 (1H, s), 8.89 (1H, t, J=6.4 Hz), 8.46 (1H, s), 8.18 (1H, s), 7.70 (1H, dd, J=8.6, 5.8 Hz), 7.22 (1H, td, J=8.2, 2.7 Hz), 7.13 (1H, dd, J=8.4, 2.6 Hz), 4.65 (2H, t, J=6.4 Hz), 4.45 (2H, d, J=6.7 Hz), 3.53 (2H, t, J=6.4 Hz), 1.84 (6H, s). HRMS (M+H) calcd for C$_{19}$H$_{20}$FN$_6$O$_5$S: 463.1200. found: 463.1195. Anal calcd for C$_{19}$H$_{19}$FN$_6$O$_5$S: C, 49.35; H, 4.14; N, 18.17. found: C, 49.55; H, 4.11; N, 17.92.

Example 6

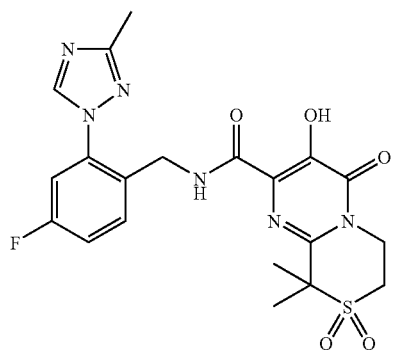

Pyrimido[2,1-c][1,4]thiazine-2-carboxamide, N-[[4-fluoro-2-(3-methyl-1H-1,2,4-triazol-1-yl)phenyl]methyl]-4,6,7,9-tetrahydro-3-hydroxy-9,9-dimethyl-4-oxo-, 8,8-dioxide: Pink solid (0.0563 g, 62%; purity: 98%). $^1$H NMR (500 MHz, CDCl$_3$) δ: 12.20 (1H, br s), 8.60 (1H, s), 8.52 (1H, br s), 7.71 (1H, t, J=6.7 Hz), 7.25-7.22 (1H, m), 7.13 (1H, d, J=7.3 Hz), 4.64 (2H, d, J=6.0 Hz), 4.49 (2H, d, J=6.4 Hz), 3.54 (2H, t, J=6.0 Hz), 2.57 (3H, s), 1.81 (6H, s). HRMS (M+H) calcd for C$_{20}$H$_{22}$FN$_6$O$_5$S: 477.1356. found: 477.1374.

Example 7

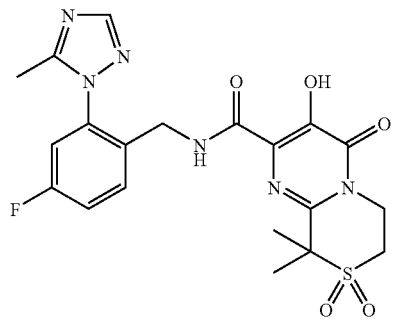

Pyrimido[2,1-c][1,4]thiazine-2-carboxamide, N-[[4-fluoro-2-(5-methyl-1H-1,2,4-triazol-1-yl)phenyl]methyl]-4,6,7,9-tetrahydro-3-hydroxy-9,9-dimethyl-4-oxo-8,8-dioxide: White solid (0.0528 g, 88%). $^1$H NMR (500 MHz, CDCl$_3$) δ: 12.21 (1H, s), 8.66 (1H, t, J=6.4 Hz), 7.68 (1H, dd, J=8.5, 6.1 Hz), 7.26-7.23 (1H, m), 7.04 (1H, dd, J=8.4, 2.6 Hz), 4.64 (2H, t, J=6.4 Hz), 4.30 (2H, d, J=6.7 Hz), 3.53 (2H, t, J=6.4 Hz), 2.49 (3H, s), 1.85 (6H, s). HRMS (M+H) calcd for C$_{20}$H$_{22}$FN$_6$O$_5$S: 477.1356. found: 477.1366. Anal calcd for C$_{20}$H$_{21}$FN$_6$O$_5$S: C, 50.41; H, 4.44; N, 17.63. found: C, 50.69; H, 4.19; N, 17.55.

Intermediate 16

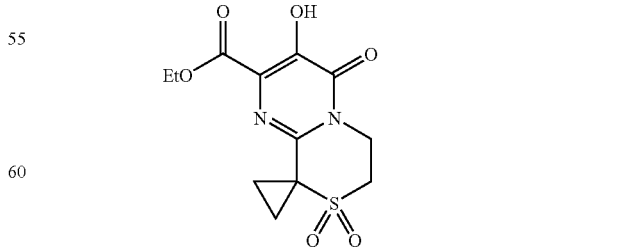

Spiro[cyclopropane-1,9'(4'H)-pyrimido[2,1-c][1,4]thiazine]-2'-carboxylic acid, 6',7'-dihydro-3'-hydroxy-4'-oxo-, ethyl ester, 8',8'-dioxide: A mixture of intermediate 12 (0.379 g, 1 mmol), 1-chloro-2-iodoethane (0.19 g, 1 mmol) and Cs₂CO₃ (0.650 g, 2 mmol) in DMF (10 mL) was stirred at room temperature for 24 h. Then, the reaction mixture was diluted with ether (50 mL), washed with water (3×10 mL), brine (10 mL), dried (Na₂SO₄), filtered and concentrated to give white solid.

A solution of above white solid in TFA (5 mL) was stirred at room temperature for 2 and concentrated. The resulting residue was purified by Prep-HPLC to afford product as off-white solid (0.184 g, 59%). ¹H NMR (500 MHz, CDCl₃) δ: 10.82 (1H, s), 4.75 (2H, t, J=6.1 Hz). HRMS (M+H) calcd for C₁₂H₁₅N₂O₆S: 315.0651. found: 315.0652.

Example 8-11 were prepared according to the procedure for Example 1 using the intermediate 16 and the appropriate amine.

Example 8

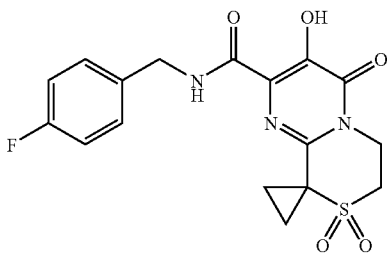

Spiro[cyclopropane-1,9'(4'H)-pyrimido[2,1-c][1,4]thiazine]-2'-carboxamide, N-[(4-fluorophenyl)methyl]-6',7'-dihydro-3'-hydroxy-4'-oxo-, 8',8'-dioxide: White solid. Yield: 0.034 g, 86%. ¹H NMR (500 MHz, CDCl₃) δ: 12.40 (1H, s), 7.58 (1H, br s), 7.31-7.28 (2H, m), 7.05 (2H, t, J=8.7 Hz), 4.78 (2H, t, J=6.1 Hz), 4.57 (2H, d, J=6.1 Hz), 3.59 (2H, t, J=6.1 Hz), 1.90 (2H, dd, J=7.9, 4.9 Hz), 1.70 (2H, dd, J=7.9, 4.9 Hz). HRMS (M+H) calcd for C₁₇H₁₇FN₃O₅S: 394.0873. found: 394.0876. Anal calcd for C₁₇H₁₆FN₃O₅S.0.5H₂O.0.2 CH₃OH: C, 50.53; H, 4.39; N, 10.28. found: C, 50.42; H, 4.11; N, 10.26.

Example 9

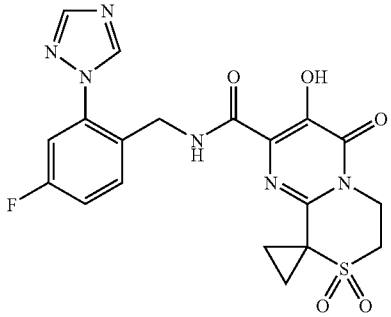

Spiro[cyclopropane-1,9'(4'H)-pyrimido[2,1-c][1,4]thiazine]-2'-carboxamide, N-[[4-fluoro-2-(1H-1,2,4-triazol-1-yl)phenyl]methyl]-6',7'-dihydro-3'-hydroxy-4'-oxo-, 8',8'-dioxide: Brown powder. Yield: 0.0255 g, 55%. ¹H NMR (500 MHz, DMSO-d₆) δ: 12.31 (1H, s), 9.29 (1H, t, J=6.3 Hz), 9.03 (1H, s), 8.32 (1H, s), 7.55-7.51 (2H, m), 7.42 (1H, td, J=8.5, 2.1 Hz), 4.56 (2H, t, J=6.0 Hz), 4.42 (2H, d, J=6.1 Hz), 3.85 (2H, t, J=6.0 Hz), 1.97 (2H, dd, J=7.8, 5.0 Hz), 1.66 (2H, dd, J=7.8, 5.0 Hz). HRMS (M+H) calcd for C₁₉H₁₈FN₆O₅S: 461.1043. found: 461.1041. Anal calcd for C₁₉H₁₇FN₆O₅S.0.5H₂O.0.3 CH₃OH: C, 48.39; H, 4.04; N, 17.54. found: C, 48.44; H, 3.30; N, 17.26.

Example 10

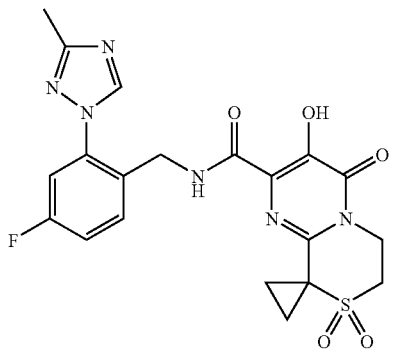

Spiro[cyclopropane-1,9'(4'H)-pyrimido[2,1-c][1,4]thiazine]-2'-carboxamide, N-[[4-fluoro-2-(3-methyl-1H-1,2,4-triazol-1-yl)phenyl]methyl]-6',7'-dihydro-3'-hydroxy-4'-oxo-, 8',8'-dioxide: Off-white solid. Yield: 0.027 g, 57%. ¹H NMR (500 MHz, CDCl₃) δ: 12.44 (1H, s), 8.75 (1H, t, J=6.1 Hz), 8.31 (1H, s), 7.66 (1H, dd, J=8.5, 6.1 Hz), 7.18 (1H, td, J=8.2, 2.8 Hz), 7.10 (1H, dd, J=8.5, 2.8 Hz), 4.76 (2H, t, J=6.1 Hz), 4.45 (2H, d, J=6.7 Hz), 3.58 (2H, t, J=6.1 Hz), 2.57 (3H, s), 1.92-1.90 (2H, m), 1.84-1.82 (2H, m). HRMS (M+H) calcd for C₂₀H₂₀FN₆O₅S: 475.1200. found: 475.1204. Anal calcd for C₂₀H₁₉FN₆O₅S: C, 50.62; H, 4.03; N, 17.71. found: C, 50.87; H, 3.98; N, 17.86.

Example 11

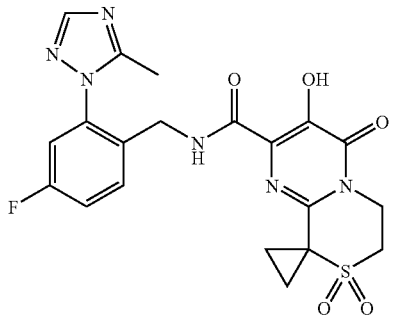

Spiro[cyclopropane-1,9'(4'H)-pyrimido[2,1-c][1,4]thiazine]-2'-carboxamide, N-[[4-fluoro-2-(5-methyl-1H-1,2,4-triazol-1-yl)phenyl]methyl]-6',7'-dihydro-3'-hydroxy-4'-oxo-, 8',8'-dioxide: Light brown powder. Yield: 0.0285 g, 60%. ¹H NMR (500 MHz, CDCl₃) δ: 12.24 (1H, s), 8.52 (1H, t, J=6.1 Hz), 8.03 (1H, s), 7.65 (1H, dd, J=8.5, 6.1 Hz), 7.26-7.21 (1H, m), 7.04 (1H, dd, J=8.4, 2.6 Hz), 4.75 (2H, t, J=6.1 Hz), 4.28 (2H, d, J=6.7 Hz), 3.57 (2H, t, J=6.1 Hz), 2.48 (3H, s), 1.95-1.93 (2H, m), 1.90-1.88 (2H, m). HRMS (M+H) calcd for C₂₀H₂₀FN₆O₅S: 475.1200. found: 475.1216. Anal calcd for $C_{20}H_{19}FN_6O_5S \cdot 0.25H_2O$: C, 50.15; H, 4.10; N, 17.55. found: C, 50.19; H, 3.76; N, 17.25.

Intermediate 17

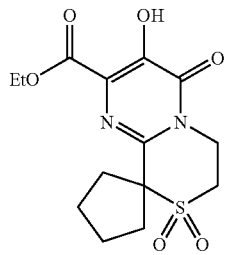

Spiro[cyclopentane-1,9'(4'H)-pyrimido[2,1-c][1,4]thiazine]-2'-carboxylic acid, 6',7'-dihydro-3'-hydroxy-4'-oxo-, ethyl ester, 8',8'-dioxide: A mixture of intermediate 12 (0.379 g, 1 mmol), 1,4-diiodobutane (0.310 g, 1 mmol) and $Cs_2CO_3$ (0.650 g, 2 mmol) in DMF (6 mL) was stirred at room temperature for 18 h. Then, the reaction mixture was diluted with ether (100 mL), washed with water (3×10 mL), brine (10 mL), dried ($Na_2SO_4$), filtered and concentrated to give viscous brown oil.

A solution of above brown oil in TFA (10 mL) was stirred at room temperature for 2 and concentrated. The resulting residue was purified by Prep-HPLC to afford product as off-white solid (0.2437 g, 71%). $^1H$ NMR (500 MHz, $CDCl_3$) δ: 10.82 (1H, s), 4.71 (2H, t, J=6.4 Hz), 4.45 (2H, q, J=7.0 Hz), 3.53 (2H, t, J=6.4 Hz), 2.62-2.48 (4H, m), 1.96-1.90 (4H, m), 1.42 (3H, t, J=7.0 Hz). HRMS (M+H) calcd for $C_{14}H_{19}N_2O_6S$: 343.0964. found: 343.0958.

Example 12-15 were prepared according to the procedure for Example 1 using the intermediate 17 and the appropriate amine.

Example 12

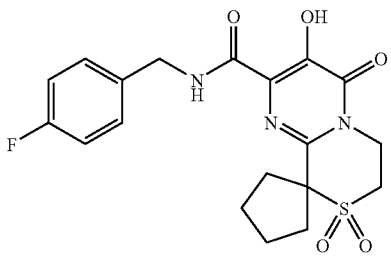

Spiro[cyclopentane-1,9'(4'H)-pyrimido[2,1-c][1,4]thiazine]-2'-carboxamide, N-[(4-fluorophenyl)methyl]-6',7'-dihydro-3'-hydroxy-4'-oxo-, 8',8'-dioxide: White solid. Yield: 0.0355 g, 84%. $^1H$ NMR (500 MHz, $CDCl_3$) δ: 12.33 (1H, s), 7.62 (1H, br t), 7.31-7.29 (2H, m), 7.06 (2H, t, J=8.5 Hz), 4.74 (2H, t, J=6.4 Hz), 4.59 (2H, d, J=6.4 Hz), 3.53 (2H, t, J=6.4 Hz), 2.63-2.58 (2H, m), 2.42-2.36 (2H, m), 1.98-1.90 (2H, m), 1.84-1.77 (2H, m). HRMS (M+H) calcd for $C_{19}H_{21}FN_3O_5S$: 422.1186. found: 422.1194. Anal calcd for $C_{19}H_{20}FN_3O_5S$: C, 54.14; H, 4.78; N, 9.97. found: C, 53.94; H, 4.46; N, 9.65.

Example 13

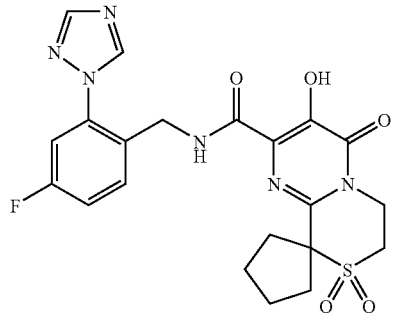

Spiro[cyclopentane-1,9'(4'H)-pyrimido[2,1-c][1,4]thiazine]-2'-carboxamide, N-[[4-fluoro-2-(1H-1,2,4-triazol-1-yl)phenyl]methyl]-6',7'-dihydro-3'-hydroxy-4'-oxo-, 8',8'-dioxide: Off-white solid. Yield: 0.043 g, 89%. $^1H$ NMR (500 MHz, $CDCl_3$) δ: 12.41 (1H, s), 8.46 (1H, s), 8.17 (1H, s), 7.71 (1H, dd, J=8.5, 5.8 Hz), 7.22 (1H, td, J=8.2, 2.4 Hz), 7.13 (1H, dd, J=8.5, 2.4 Hz), 4.73 (2H, t, J=6.4 Hz), 3.52 (2H, t, J=6.4 Hz), 2.65-2.60 (2H, m), 2.54-2.48 (2H, m), 1.98-1.89 (4H, m). HRMS (M+H) calcd for $C_{21}H_{22}FN_6O_5S$: 489.1356. found: 489.1362. Anal calcd for $C_{21}H_{21}FN_6O_5S$: C, 51.63; H, 4.33; N, 17.20. found: C, 51.64; H, 4.13; N, 16.92.

Example 14

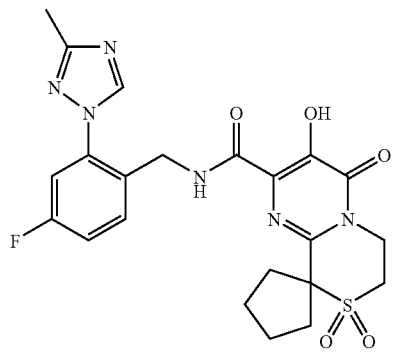

Spiro[cyclopentane-1,9'(4'H)-pyrimido[2,1-c][1,4]thiazine]-2'-carboxamide, N-[[4-fluoro-2-(3-methyl-1H-1,2,4-triazol-1-yl)phenyl]methyl]-6',7'-dihydro-3'-hydroxy-4'-oxo-, 8',8'-dioxide: White solid. Yield: 0.0408 g, 81%. $^1H$ NMR (500 MHz, $CDCl_3$) δ: 12.60 (1H, s), 8.61 (1H, t, J=6.4 Hz), 8.30 (1H, s), 7.69 (1H, dd, J=8.5, 6.1 Hz), 7.17 (1H, td, J=8.2, 2.4 Hz), 7.09 (1H, dd, J=8.5, 2.4 Hz), 4.74 (2H, t, J=6.4 Hz), 4.49 (2H, d, J=6.7 Hz), 3.52 (2H, t, J=6.4 Hz), 2.66-2.60 (2H, m), 2.53 (3H, s), 2.52-2.47 (2H, m), 1.96-1.79 (4H, m). HRMS (M+H) calcd for $C_{22}H_{24}FN_6O_5S$: 503.1513. found: 503.1529. Anal calcd for $C_{22}H_{23}FN_6O_5S$: C, 52.58; H, 4.61; N, 16.72. found: C, 52.31; H, 4.43; N, 16.44.

Example 15

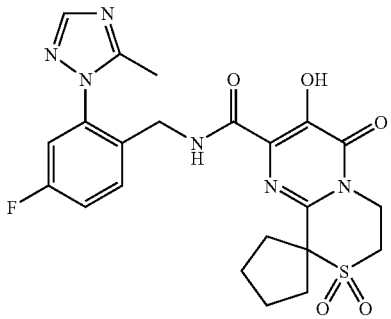

Spiro[cyclopentane-1,9'(4'H)-pyrimido[2,1-c][1,4]thiazine]-2'-carboxamide, N-[[4-fluoro-2-(5-methyl-1H-1,2,4-triazol-1-yl)phenyl]methyl]-6',7'-dihydro-3'-hydroxy-4'-oxo-, 8',8'-dioxide: White solid. Yield: 0.0458 g, 91%: $^1$H NMR (500 MHz, CDCl$_3$) δ: 12.38 (1H, s), 8.69 (1H, t, J=6.4 Hz), 7.98 (1H, s), 7.68 (1H, dd, J=8.5, 6.1 Hz), 7.24 (1H, td, J=8.1, 2.4 Hz), 7.03 (1H, dd, J=8.5, 2.4 Hz), 4.72 (2H, t, J=6.4 Hz), 4.28 (2H, d, J=6.7 Hz), 3.52 (2H, t, J=6.4 Hz), 2.66-2.60 (2H, m), 2.55-2.50 (2H, m), 2.50 (3H, s), 1.99-1.89 (4H, m). HRMS (M+H) calcd for C$_{22}$H$_{24}$FN$_6$O$_5$S: 503.1513. found: 503.1531. Anal calcd for C$_{22}$H$_{23}$FN$_6$O$_5$S: C, 52.58; H, 4.61; N, 16.72. found: C, 52.28; H, 4.36; N, 16.38.

Intermediate 18

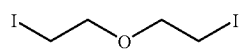

2-Iodoethyl ether: To a stirred solution of 2-chloroethyl ether (14.3 g, 100 mmol) in anhydrous acetone (200 mL) was added powder NaI (65 g, 433.6 mmol). The resulting clear yellow solution was heated at reflux for five days. Then, cooled, filtered through a plug of celite and concentrated to give yellow liquid. This was taken up in ether (200 mL) washed with water (50 mL) and 10% aq. NaHSO3 (2×10 mL), dried (Na2SO4), filtered and concentrated to afford product (32.45 g, 100%) as colorless liquid. $^1$H NMR (500 MHz, CDCl$_3$) δ: 3.77 (4H, t, J=6.9 Hz), 3.26 (4H, t, J=6.9 Hz).

Intermediate 19

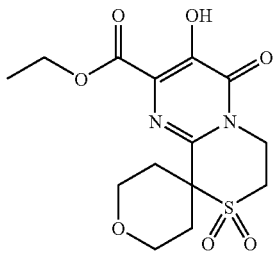

Spiro[4H-pyran-4,9'(4'H)-pyrimido[2,1-c][1,4]thiazine]-2'-carboxylic acid, 2,3,5,6,6',7'-hexahydro-3'-hydroxy-4'-oxo-, ethyl ester, 8',8'-dioxide: To a stirred yellow mixture of intermediate 12 (0.189 g, 0.50 mmol) intermediate 18 (0.208 g, 0.62 mmol) in DMF (5 mL) wad added Cs$_2$CO$_3$ (0.332 g, 1.02 mmol) at once at room temperature. After 24 h, the reaction mixture was diluted with Et$_2$O (50 mL), washed with water (2×10 mL), brine (10 mL), dried (Na$_2$SO$_4$), filtered and concentrated to give colorless paste which was used in the subsequent step without purification.

A solution of above paste in trifluoroacetic acid (3 mL) was stirred at room temperature for 1.5 h and concentrated to afford an yellow residue which was triturated with ether to give product as off-white solid (0.0909 g, 51%). $^1$H NMR (500 MHz, CDCl$_3$) δ: 10.79 (1H, s), 4.67 (2H, t, J=6.1 Hz), 4.46 (2H, q, J=7.0 Hz), 4.03-3.99 (4H, m), 3.53 (2H, t, J=6.4 Hz), 2.52-2.46 (2H, m), 2.22-2.17 (2H, m), 1.43 (3H, t, J=7.0 Hz). HRMS (M+H) calcd for C$_{14}$H$_{19}$N$_2$O$_7$S: 359.0913. found: 359.0915.

Example 16-18 were prepared according to the procedure for Example 4 using the intermediate 19 and the appropriate amine.

Example 16

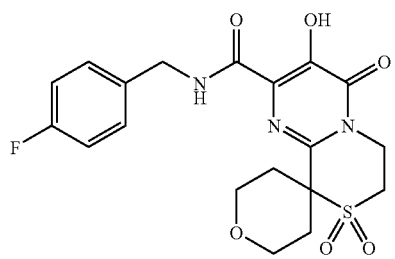

Spiro[4H-pyran-4,9'(4'H)-pyrimido[2,1-c][1,4]thiazine]-2'-carboxamide, N-[(4-fluorophenyl)methyl]-2,3,5,6,6',7'-hexahydro-3'-hydroxy-4'-oxo-, 8',8'-dioxide: White solid (0.0314 g, 86%). $^1$H NMR (500 MHz, CDCl$_3$) δ: 12.42 (1H, s), 7.50 (1H, t, J=5.6 Hz), 7.33-7.30 (2H, m), 7.07 (2H, t, J=8.7 Hz), 4.74 (2H, t, J=6.4 Hz), 4.60 (2H, d, J=6.1 Hz), 4.06-4.02 (2H, m), 3.80-3.75 (2H, m), 3.54 (2H, t, J=6.4 Hz), 2.52-2.46 (2H, m), 2.33-2.28 (2H, m). HRMS (M+H) calcd for C$_{19}$H$_{21}$FN$_3$O$_6$S: 438.1135. found: 438.1153. Anal calcd for C$_{19}$H$_{20}$FN$_3$O$_6$S: C, 52.16; H, 4.60; N, 9.60. found: C, 51.91; H, 4.52; N, 9.36.

Example 17

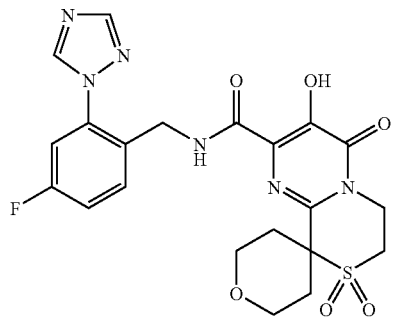

Spiro[4H-pyran-4,9'(4'H)-pyrimido[2,1-c][1,4]thiazine]-2'-carboxamide, N-[[4-fluoro-2-(1H-1,2,4-triazol-1-yl)phenyl]methyl]-2,3,5,6,6',7'-hexahydro-3'-hydroxy-4'-oxo-, 8',8'-dioxide: White solid (0.0335 g, 79%). $^1$H NMR (500 MHz, CDCl$_3$) δ: 12.54 (1H, s), 8.78 (1H, t, J=6.0 Hz), 8.46 (1H, s), 8.23 (1H, s), 7.73 (1H, dd, J=8.6, 5.8 Hz), 7.23 (1H, td, J=8.6, 2.5 Hz), 7.14 (1H, dd, J=8.6, 2.5 Hz), 4.73 (2H, t, J=6.4 Hz), 4.46 (2H, d, J=6.7 Hz), 4.07-4.03 (2H, m), 3.91-

3.86 (2H, m), 3.53 (2H, t, J=6.4 Hz), 2.54-2.48 (2H, m), 2.44-2.39 (2H, m). HRMS (M+H) calcd for $C_{21}H_{22}FN_6O_6S$: 505.1306. found: 505.1320. Anal calcd for $C_{21}H_{21}FN_6O_6S$: C, 49.99; H, 4.19; N, 16.65. found: C, 49.76; H, 3.96; N, 16.36.

Example 18

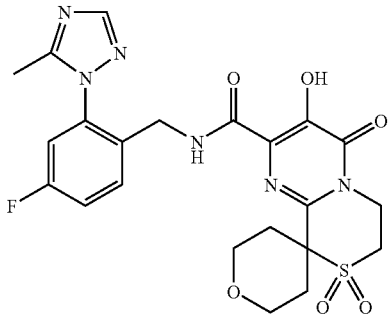

Spiro[4H-pyran-4,9'(4'H)-pyrimido[2,1-c][1,4]thiazine]-2'-carboxamide, N-[[4-fluoro-2-(5-methyl-1H-1,2,4-triazol-1-yl)phenyl]methyl]-2,3,5,6,6',7'-hexahydro-3'-hydroxy-4'-oxo-, 8',8'-dioxide: White solid (0.0349 g, 80%). $^1$H NMR (500 MHz, CDCl$_3$) δ: 12.51 (1H, s), 8.58 (1H, t, J=6.4 Hz), 8.04 (1H, s), 7.70 (1H, dd, J=8.6, 5.8 Hz), 7.24 (1H, td, J=8.6, 2.4 Hz), 7.04 (1H, dd, J=8.2, 2.4 Hz), 4.73 (2H, 6.4 Hz), 4.30 (2H, d, J=6.7 Hz), 4.08-4.04 (2H, m), 3.90-3.85 (2H, m), 3.53 (2H, t, J=6.4 Hz), 2.54-2.48 (2H, m), 2.50 (3H, s), 2.45-2.41 (2H, m). HRMS (M+H) calcd for $C_{22}H_{24}FN_6O_6S$: 519.1462. found: 519.1443. Anal calcd for $C_{22}H_{23}FN_6O_6S$: C, 50.96; H, 4.47; N, 16.20. found: C, 50.97; H, 4.19; N, 15.91.

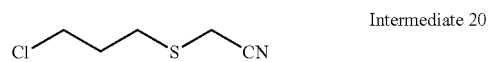

Intermediate 20

2-(3-chloropropylthio)acetonitrile: To a stirred solution of 3-chloro-1-propanethiol (20 g, 180.8 mmol) and chloroacetonitrile (12.6 mL, 200 mmol) in THF (150 mL) was added $K_3CO_3$ (27.6 g, 200 mmol). After 24 h at room temperature, the reaction mixture was filtered through a silica gel plug and the plug was washed with ether (100 mL). The filtrate was concentrated to give colorless liquid (9.905 g, 37%) which was used in the next step without purification. $^1$H NMR (500 MHz, CDCl$_3$) δ: 3.67 (2H, t, J=6.1 Hz), 3.31 (2H, s), 2.92 (2H, t, J=7.0 Hz), 2.15-2.10 (2H, m).

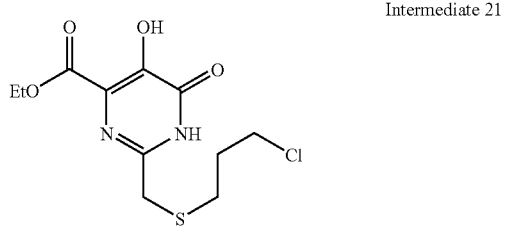

Intermediate 21

Ethyl 2-((3-chloropropylthio)methyl)-5-hydroxy-6-oxo-1,6-dihydropyrimidine-4-carboxylate: To a stirred solution of intermediate 20 (9.9 g, 66.15 mmol) in ethanol (50 mL) was added 50% aq. hydroxylamine (4.3 mL, 70 mmol). After 15 h, the reaction mixture was cooled in an ice-water bath and diethyl acetylenedicarboxylate was slowly added via syringe. The cold bath was removed and stirred for 1 h at room temperature and concentrated to give yellow residue. This was taken up in ether (200 mL), washed with water (50 mL), brine (50 mL), dried (Na$_2$SO$_4$), filtered and concentrated to give yellow oil (25.9 g).

A xylenes (300 mL) solution of above yellow oil was heated at reflux for 15 and then, cooled and extracted with 0.5 M aq. Na$_2$CO$_3$ (4×50 mL). The combine aq. layers were extracted with EtOAc (2×50 mL) and organic layers discarded. The aq. layer was acidified with conc. HCl and extracted with CH$_2$Cl$_2$ (4×50 mL). The combined CH$_2$Cl$_2$ extracts dried (Na$_2$SO$_4$), filtered and concentrated to afford brown powder (5.0 g, 25%). $^1$H NMR (500 MHz, CDCl$_3$) δ: 11.40 (1H, br s), 10.94 (1H, s), 4.51 (2H, q, J=7.0 Hz), 3.70 (2H, s), 3.61 (2H, t, J=6.1 Hz), 2.70 (2H, t, J=7.0 Hz) 2.07-2.02 (2H, m), 1.44 (3H, t, J=7.0 Hz). LCMS (M+H) calcd for $C_{11}H_{16}ClN_2O_4S$: 307.05. found: 307.09.

Example 19

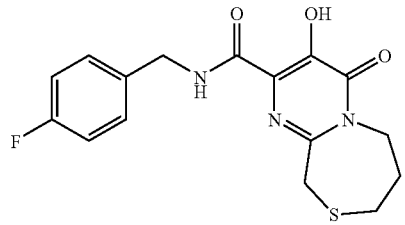

N-(4-Fluorobenzyl)-3-hydroxy-4-oxo-6,7,8,10-tetrahydro-4H-pyrimido[2,1-c][1,4]thiazepine-2-carboxamide: A mixture of intermediate 21 (0.202 g, 0.6563 mmol) and K$_2$CO$_3$ (0.28 g, 2 mmol) in DMF was heated at 90° C. for 1 h and cooled to room temperature. 4-Fluorobenzylamine (1.25 g, 10 mmol) was added and heated at 110° C. for 18 h. After this, cooled and purified by Prep-HPLC to afford product as a white solid (0.0919 g, 40%). $^1$H NMR (500 MHz, CDCl$_3$) δ: 12.06 (1H, s), 7.83 (1H, br t), 7.32-7.29 (2H, m), 7.04 (2H, t, J=8.5 Hz), 4.56 (2H, d, J=6.1 Hz), 4.36-4.33 (2H, m), 3.77 (2H, s), 2.90 (2H, t, J=5.6 Hz), 2.15-2.11 (2H, m). HRMS (M+H) calcd for $C_{16}H_{17}FN_3O_3S$: 350.0975. found: 350.0959. Anal calcd for $C_{16}H_{16}FN_3O_3S·0.5C_{16}H_{15}FN_3O_3S$: C, 56.39; H, 4.73; N, 11.51. found: 56.42; H, 4.27; N, 11.23.

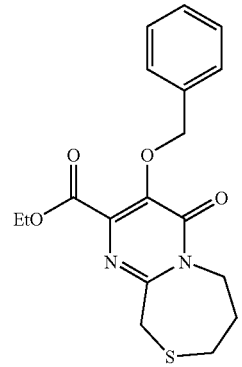

Intermediate 22

Ethyl 3-(benzyloxy)-4-oxo-6,7,8,10-tetrahydro-4H-pyrimido[2,1-c][1,4]thiazepine-2-carboxylate: A mixture of intermediate 21 (5 g, 16.2446 mmol) and K$_2$CO$_3$ (4.5 g, 32.5 mmol) in DMF (150 mL) was placed in a preheated oil bath and stirred for 1.5 h. After this, benzyl bromide (2.4 mL, 20 mmol) was added and continued stirring for additional 3 h. Then, the reaction mixture was cooled, diluted with ether (250 mL), washed with water (3×50 mL). The combine aq. layers extracted with ether (4×100 mL) and combined with previous organic phase, and washed with brine (50 mL). The organic layer was dried (Na$_2$SO$_4$/activated carbon), filtered and concentrated to give viscous paste. Crystallization of this paste from CH$_2$Cl$_2$/hexanes provided product as white solid (4.3827 g, 75%). $^1$H NMR (500 MHz, CDCl$_3$) δ: 7.48-7.46 (2H, m), 7.37-7.30 (3H, m), 5.25 (2H, s), 4.36-4.31 (4H, m), 3.89 (2H, s), 2.94 (2H, t, J=5.6 Hz), 2.16-2.12 (2H, m), 1.30 (3H, t, J=7.0 Hz). HRMS (M+H) calcd for C$_{18}$H$_{21}$N$_2$O$_4$S: 361.1222. found: 361.1221.

mmol) in TFA (2 mL) was stirred for 18 h at room temperature and then concentrated to give yellow residue. This was dissolved in DMF/EtOH (1:1, 2 mL) and heated with 4-fluorobenzylamine (0.125 g, 1 mmol) and Et$_3$N (0.14 mL, 1 mmol) in a sealed vial at 100° C. for 6 h. Then, cooled and purified by Prep-HPLC to afford product as off-white powder (0.0146 g, 72%) $^1$H NMR (500 MHz, CDCl$_3$) δ: 12.00 (1H, br s), 7.81 (1H, s), 7.32-7.29 (2H, m), 7.05 (2H, t, J=8.5 Hz), 5.22-5.18 (1H, m), 4.58 (2H, d, J=6.1 Hz), 4.15 (1H, q, J=7.0 Hz), 3.58 (1H, dd, J=13.7, 11.9 Hz), 3.12-3.06 (1H, m), 2.76 (1H, dt, J=14.7, 4.3 Hz), 2.35-2.29 (1H, m), 1.91-1.83 (1H, m), 1.57 (3H, d, J=7.0 Hz). HRMS (M+H) calcd for C$_{17}$H$_{19}$FN$_3$O$_3$S: 364.1131. found: 364.1133.

Intermediate 23

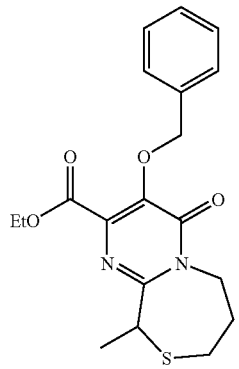

Intermediate 24

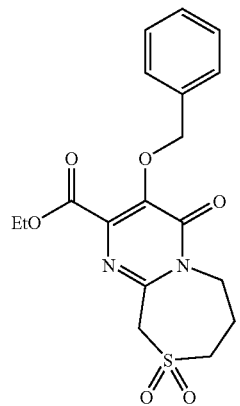

Ethyl 3-(benzyloxy)-10-methyl-4-oxo-6,7,8,10-tetrahydro-4H-pyrimido[2,1-c][1,4]thiazepine-2-carboxylate: To a stirred solution of intermediate 22 (0.180 g, 0.5 mmol) and iodomethane (0.62 mL, 10 mmol) in THF (5 mL) at −78 C was added 1M solution of LiHMDS (1 mL, 1 mmol) over 2 minutes. After 1.5 h, the reaction mixture was quenched with saturated aq. NH$_4$Cl (three drops), diluted with EtOAc (50 mL), dried (Na$_2$SO$_4$), filtered, concentrated and the residue was purified by Prep-HPLC to afford desired product as orange solid (0.021 g, 11%). $^1$H NMR (500 MHz, CDCl$_3$) δ: 7.48-7.46 (2H, m), 7.37-7.29 (3H, m), 5.24 (2H, s), 5.15 (1H, dd, J=13.9, 4.4 Hz), 4.33 (2H, q, J=7.0 Hz), 4.18 (1H, q, J=7.0 Hz), 3.62 (1H, dd, J=13.6, 12.1 Hz), 3.14-3.09 (1H, m), 2.77 (1H, dt, J=14.4, 4.2 Hz), 2.34-2.27 (1H, m), 1.91-1.82 (1H, m), 1.62 (3H, d, J=7.0 Hz), 1.30 (3H, t, J=7.0 Hz). HRMS (M+H) calcd for C$_{19}$H$_{23}$N$_2$O$_4$S: 375.1379. found: 375.1375.

6H-Pyrimido[2,1-c][1,4]thiazepine-2-carboxylic acid, 4,7,8,10-tetrahydro-4-oxo-3-(phenylmethoxy)-, ethyl ester, 9,9-dioxide: To a stirred solution of intermediate 22 (1.894 g, 5.255 mmol) in CH$_2$Cl$_2$ (50 mL) was added mCPBA (57-86%, 3.70 g, 15 mmol) at once. After 1.5 h, saturated NaHCO$_3$ (20 mL) and 10% Na$_2$S$_2$O$_3$ (10 mL) were added and stirred for additional 20 minutes. Then, the organic layer separated, washed successively with saturated aq. NaHCO$_3$ (20 mL), brine (10 mL), dried (Na$_2$SO$_4$), filtered and concentrated to give paste which was crystallized from CH$_2$Cl$_2$/hexanes to afford product as white solid (2.0501 g, 99%). $^1$H NMR (500 MHz, CDCl$_3$) δ: 7.46-7.45 (2H, m), 7.37-7.31 (3H, m), 5.25 (2H, s), 4.60 (2H, s), 4.47-4.41 (2H, m), 4.34 (2H, q, J=7.0 Hz), 3.39 (2H, t, J=6.1 Hz), 2.38-2.33 (2H, m), 1.31 (3H, t, J=7.0 Hz). HRMS (M+H) calcd for C$_{18}$H$_{21}$N$_2$O$_6$S: 393.1120. found: 393.1136.

Example 20

Example 21

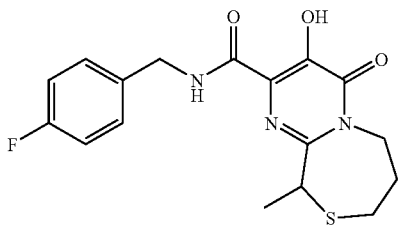

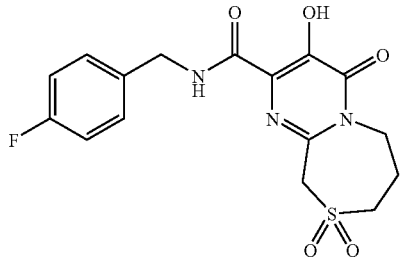

N-(4-Fluorobenzyl)-3-hydroxy-10-methyl-4-oxo-6,7,8,10-tetrahydro-4H-pyrimido[2,1-c][1,4]thiazepine-2-carboxamide: A solution of intermediate 23 (0.021 g, 0.056

6H-Pyrimido[2,1-c][1,4]thiazepine-2-carboxamide, N-[(4-fluorophenyl)methyl]-4,7,8,10-tetrahydro-3-hydroxy-4-oxo-, 9,9-dioxide: A solution of intermediate 24 (0.363 g, 0.925 mmol) in TFA (10 mL) was stirred at for 3 h at 25-35° C. and then concentrated to give yellow residue which provided product as white powder (71.4 mg, 24%) upon trituration with EtOAc.

A suspension of above white powder and 4-fluorobenzylamine (0.5 mL, 4.38 mmol) in EtOH/DMF (1:1, 10 mL) was heated at 80° C. for 4 h. Then, the reaction mixture was concentrated and the resulting residue was purified by Prep-HPLC to afford product as white powder (0.035 g, 39%). $^1$H NMR (500 MHz, DMSO-d$_6$) δ: 12.46 (1H, s), 9.64 (1H, t, J=6.4 Hz), 7.38-7.36 (2H, m), 4.92-4.75 (2H, br s), 4.46 (2H, d, J=6.4 Hz), 3.60 (2H, t, J=5.2 Hz), 3.31 (2H, s), 2.14-2.07 (2H, br s) HRMS (M+H) calcd for $C_{16}H_{17}FN_3O_5S$: 382.0873. found: 382.0886. Anal calcd for $C_{16}H_{16}FN_3O_5S.0.13$ TFA: C, 49.29; H, 4.10; N, 10.61. found: C, 49.67; H, 3.70; N, 10.67.

Example 22

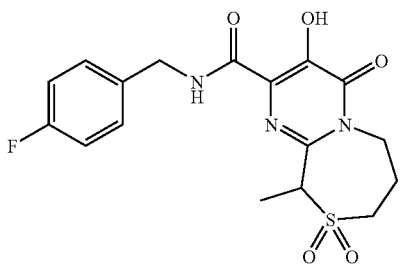

6H-Pyrimido[2,1-c][1,4]thiazepine-2-carboxamide, N-[(4-fluorophenyl)methyl]-4,7,8,10-tetrahydro-3-hydroxy-10-methyl-4-oxo-, 9,9-dioxide: To a stirred solution of intermediate 24 (0.196 g, 0.50 mmol) and iodomethane (0.42 mL, 6.7 mmol) in THF at −78° C. was added 1M LiHMDS/THF (1.1 mL, 1.1 mmol) over 5 minutes. The resulting orange reaction mixture was stirred overnight (16 h) while slowing allowing to warm to ambient temperature. Then, quenched with sat. NH$_4$Cl (3 drops), diluted with ether (50 mL), dried (Na$_2$SO$_4$), filtered and concentrated to give the product as yellow paste.

The above yellow paste was stirred in TFA (10 mL) for 3 h at room temperature and concentrated to afford crude debenzylated product. This was dissolved in EtOH/DMF (1:1, 6 mL) and heated with 4-fluorobenzylamine (0.50 g, 4 mmoL) and Et$_3$N (0.14 mL, 1 mmol) at 110 C in sealed vial for 4 h. Then, the reaction mixture was cooled and purified by Prep-HPLC to provide product as white powder (0.0803 g, 41%). $^1$H NMR (500 MHz, DMSO-d$_6$) δ: 12.52 (1H, s), 9.27 (1H, t, J=6.4 Hz), 7.39-7.36 (2H, m), 7.17 (2H, t, J=8.9 Hz), 5.33 (1H, q, J=7.0 Hz), 4.95 (1H, dd, J=14.7, 6.1 Hz), 4.54-4.46 (2H, m), 4.02 (1H, dd, J=14.6, 11.0 Hz), 3.77-3.71 (1H, m), 3.45 (1H, dt, J=14.3, 3.7 Hz), 2.41-2.35 (1H, m), 1.83-1.74 (1H, m), 1.67 (3H, d, J=7.0 Hz). HRMS (M+H) calcd for $C_{17}H_{19}FN_3O_5S$: 396.1029. found: 396.1016. Anal calcd for $C_{17}H_{18}FN_3O_5S.0.33H_2O$: C, 50.87; H, 4.69; N, 10.47. found: C, 51.18; H, 4.80; N, 10.40.

Example 23

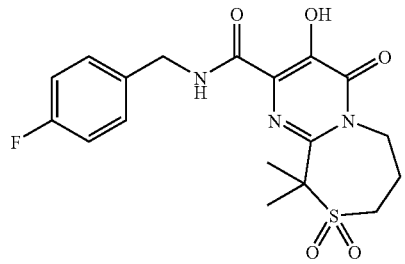

6H-Pyrimido[2,1-c][1,4]thiazepine-2-carboxamide, N-[(4-fluorophenyl)methyl]-4,7,8,10-tetrahydro-3-hydroxy-10,10-dimethyl-4-oxo-, 9,9-dioxide: A mixture of intermediate 24 (0.098 g, 0.25 mmol), iodomethane (0.12 mL, 2 mmol) and Cs$_2$CO$_3$ (0.325 g, 1 mmol) in DMF (3 mL) was stirred at room temperature for 6 h, diluted with EtOAc (50 mL), washed with water (3×10 mL), brine (10 mL), dried (Na$_2$SO$_4$), filtered and concentrated to give orange solid.

The above orange solid was stirred with TFA (8 mL) for 3 h at room temperature and concentrated to give yellow solid. This yellow solid was dissolved in EtOH/DMF (1:1, 3 mL) and heated with 4-fluorobenzylamine (0.25 g, 2 mmol) and Et$_3$N (0.07 mL, 0.5 mmol) at 110° C. for 6 h in a sealed vial. Then, cooled and purified by Prep-HPLC to afford product as brown solid (0.0492 g, 48%). $^1$H NMR (500 MHz, CDCl$_3$) δ: 12.20 (1H, s), 7.63 (1H, br s), 7.32-7.29 (2H, m), 7.05 (2H, t, J=8.5 Hz), 4.73-4.65 (2H, br s), 4.58 (2H, d, J=5.5 Hz), 3.46 (2H, t, J=5.8 Hz), 2.33-2.28 (2H, m), 1.90 (6H, s). HRMS (M+H) calcd for $C_{18}H_{21}FN_3O_5S$: 410.1186. found: 410.1203. Anal calcd for $C_{18}H_{20}FN_3O_5S.1.0H_2O$: C, 50.58; H, 5.19; N, 9.83. found: C, 50.45; H, 4.98; N, 9.83.

Example 24

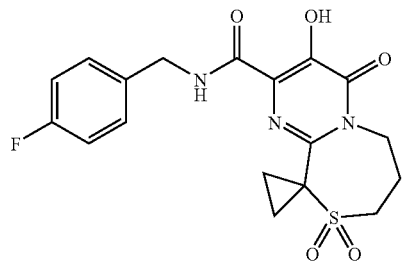

Spiro[cyclopropane-1,10'(4'H)-[6H]pyrimido[2,1-c][1,4]thiazepine]-2'-carboxamide, N-[(4-fluorophenyl)methyl]-7',8'-dihydro-3'-hydroxy-4'-oxo-, 9',9'-dioxide: A mixture of intermediate 24 (0.098 g, 0.25 mmol), 1-chloro-1iodoethane (0.190 g, 1 mmol) and Cs$_2$CO$_3$ (0.325 g, 1 mmol) in DMF (3 mL) was stirred at room temperature for 24 h, diluted with EtOAc (50 mL), washed with water (3×10 mL), brine (10 mL), dried (Na$_2$SO$_4$), filtered and concentrated to give yellow solid.

The above orange solid was stirred with TFA (5 mL) for 1 h at room temperature and concentrated to give yellow solid. This yellow solid was dissolved in EtOH/DMF (1:1, 3 mL) and heated with 4-fluorobenzylamine (0.125 g, 1 mmol) and Et$_3$N (0.14 mL, 1 mmol) at 110° C. for 4 h in a sealed vial.

Then, cooled and purified by Prep-HPLC to afford product as brown solid (0.0418 g, 41%). $^1$H NMR (500 MHz, CDCl$_3$) δ: 12.41 (1H, s), 7.76 (1H, br s), 7.32-7.29 (2H, m), 7.05 (2H, t, J=8.5 Hz), 4.62-4.47 (2H, m), 4.57 (2H, d, J=6.1 Hz), 3.32 (2H, t, J=6.1 Hz), 2.40-2.36 (2H, m), 1.96-1.93 (2H, br s), 1.72-1.68 (2H, br s) HRMS (M+H) calcd for C$_{18}$H$_{19}$FN$_3$O$_5$S: 408.1029. found: 408.1037. Anal calcd for C$_{18}$H$_{18}$FN$_3$O$_5$S: C, 53.06; H, 4.45; N, 10.31. found: C, 53.07; H, 4.30; N, 10.24.

Example 25

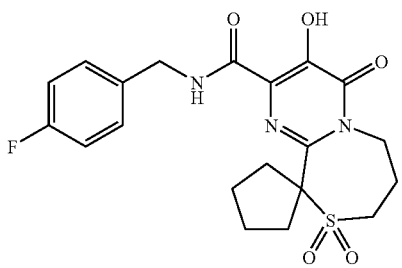

Spiro[cyclopentane-1,10'(4'H)-[6H]pyrimido[2,1-c][1,4]thiazepine]-2'-carboxamide, N-[(4-fluorophenyl)methyl]-7',8'-dihydro-3'-hydroxy-4'-oxo-, 9',9'-dioxide: A mixture of intermediate 24 (0.098 g, 0.25 mmol), 1,4-diiodobutane (0.04 mL, 0.3 mmol) and Cs$_2$CO$_3$ (0.325 g, 1 mmol) in DMF (3 mL) was stirred at room temperature for 8 h, diluted with EtOAc (50 mL), washed with water (2×10 mL), brine (10 mL), dried (Na$_2$SO$_4$), filtered and concentrated to give yellow solid.

The above orange solid was stirred with TFA (5 mL) for 3 h at room temperature and concentrated to give yellow solid. This yellow solid was dissolved in EtOH/DMF (2:1, 3 mL) and heated with 4-fluorobenzylamine (0.16 g, 1.28 mmol) and Et$_3$N (0.14 mL, 1 mmol) at 110° C. for 4 h in a sealed vial. Then, cooled and purified by Prep-HPLC to afford product as brown solid (0.0754 g, 69%). $^1$H NMR (500 MHz, CDCl$_3$) δ: 12.25 (1H, s), 7.64 (1H, br s), 7.32-7.29 (2H, m), 7.05 (2H, t, J=8.5 Hz), 4.65-4.59 (2H, m), 4.59 (2H, d, J=6.4 Hz), 3.43 (2H, t, J=6.1 Hz), 2.74-2.62 (4H, m), 2.28-2.24 (2H, m), 2.00-1.92 (2H, m), 1.79-1.71 (2H, m). HRMS (M+H) calcd for C$_{20}$H$_{23}$FN$_3$O$_5$S: 436.1342. found: 436.1350. Anal calcd for C$_{20}$H$_{22}$FN$_3$O$_5$S: C, 55.16; H, 5.09; N, 9.65. found: C, 55.93; H, 5.18; N, 9.59.

Intermediate 25

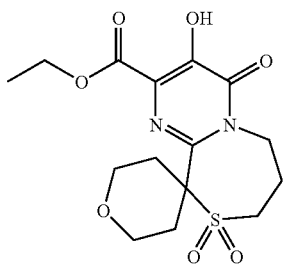

Spiro[4H-pyran-4,10'(4'H)-[6H]pyrimido[2,1-c][1,4]thiazepine]-2'-carboxylic acid, 2,3,5,6,7',8'-hexahydro-3'-hydroxy-4'-oxo-, ethyl ester, 9',9'-dioxide: To a stirred yellow mixture of intermediate 19/24 (0.1942 g, 0.50 mmol) intermediate 18 (0.208 g, 0.62 mmol) in DMF (5 mL) wad added Cs$_2$CO$_3$ (0.332 g, 1.02 mmol) at once at room temperature. After 24 h, the reaction mixture was diluted with Et$_2$O (50 mL), washed with water (2×10 mL), brine (10 mL), dried (Na$_2$SO$_4$), filtered and concentrated to give colorless paste which was used in the subsequent step without purification.

A solution of above paste in trifluoroacetic acid (3 mL) was stirred at room temperature for 2 h and concentrated to afford an yellow residue which was triturated with CH$_2$Cl$_2$/hexanes to give product as white solid (0.1113 g, 60%). $^1$H NMR (500 MHz, CDCl$_3$) δ: 10.71 (1H, s), 4.74-4.58 (2H, br s), 4.43 (2H, q, J=7.0 Hz), 4.07-4.01 (2H, m), 3.82-3.72 (2H, m), 3.42-3.36 (2H, m), 2.63-2.52 (4H, m), 2.33-2.26 (2H, m), 1.41 (3H, t, J=7.0 Hz). HRMS (M+H) calcd for C$_{15}$H$_{21}$N$_2$O$_7$S: 373.1069. found: 373.1058.

Example 26-29 were prepared according to the procedure for Example 4 using the intermediate 25 and the appropriate amine.

Example 26

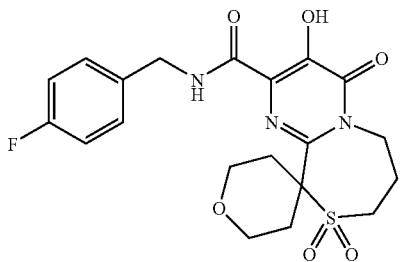

Spiro[4H-pyran-4,10'(4'H)-[6H]pyrimido[2,1-c][1,4]thiazepine]-2'-carboxamide, N-[(4-fluorophenyl)methyl]-2,3,5,6,7',8'-hexahydro-3'-hydroxy-4'-oxo-, 9',9'-dioxide: Off-white solid (0.020 g, 83%; purity: 93%). $^1$H NMR (500 MHz, CDCl$_3$) δ: 12.28 (1H, s), 7.38 (1H, t, J=5.5 Hz), 7.30 (2H, dd, J=8.6, 5.2 Hz), 7.07 (2H, t, J=8.7 Hz), 4.83-4.61 (2H, brs), 4.58 (2H, d, J=5.8 Hz), 4.02 (2H, dt, J=11.6, 3.7 Hz), 3.67-3.58 (2H, m), 3.39-3.35 (2H, m), 2.61-2.52 (4H, m), 2.31-2.25 (2H, m). HRMS (M+H) calcd for C$_{20}$H$_{23}$FN$_3$O$_6$S: 452.1292. found: 452.1276.

Example 27

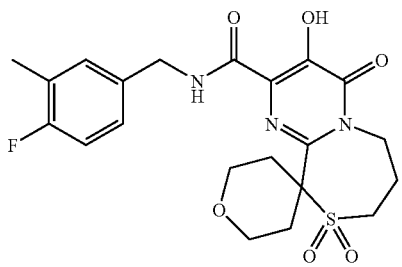

Spiro[4H-pyran-4,10'(4'H)-[6H]pyrimido[2,1-c][1,4]thiazepine]-2'-carboxamide, N-[(4-fluoro-3-methylphenyl)methyl]-2,3,5,6,7',8'-hexahydro-3'-hydroxy-4'-oxo-, 9',9'-dioxide: Light purple solid (0.0229 g, 92%; purity: 95%). $^1$H NMR (500 MHz, CDCl$_3$) δ: 12.30 (1H, s), 7.36 (1H, t, J=5.5 Hz), 7.15-7.07 (2H, m), 7.00 (1H, t, J=8.9 Hz), 4.90-4.56 (2H, br), 4.53 (2H, d, J=5.8 Hz), 4.02 (2H, dt, J=11.6, 3.7 Hz), 3.67-3.58 (2H, m), 3.39-3.35 (2H, m), 2.61-2.52 (4H, m), 2.30-2.25 (5H, m). HRMS (M+H) calcd for $C_{21}H_{25}FN_3O_6S$: 466.1448. found: 466.1469.

Example 28

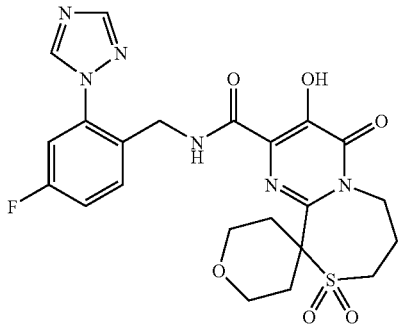

Spiro[4H-pyran-4,10'(4'H)-[6H]pyrimido[2,1-c][1,4]thiazepine]-2'-carboxamide, N-[[4-fluoro-2-(1H-1,2,4-triazol-1-yl)phenyl]methyl]-2,3,5,6,7',8'-hexahydro-3'-hydroxy-4'-oxo-, 9',9'-dioxide: White solid (0.0175 g, 63%; purity: 97%). $^1$H NMR (500 MHz, CDCl$_3$) δ: 12.49 (1H, s), 8.64 (1H, t, J=6.4 Hz), 8.45 (1H, s), 8.16 (1H, s), 7.72 (1H, dd, J=8.6, 5.8 Hz), 7.23 (1H, td, J=8.2, 2.4 Hz), 7.13 (1H, dd, J=8.5, 2.4 Hz), 4.92-4.52 (2H, br), 4.44 (2H, d, J=6.7 Hz), 4.02 (H, dt, J=11.6, 3.7 Hz), 3.70-3.60 (2H, m), 3.40-3.34 (2H, m), 2.72-2.57 (4H, m), 2.30-2.24 (2H, m). HRMS (M+H) calcd for $C_{22}H_{24}FN_6O_6S$: 519.1462. found: 519.1480.

Example 29

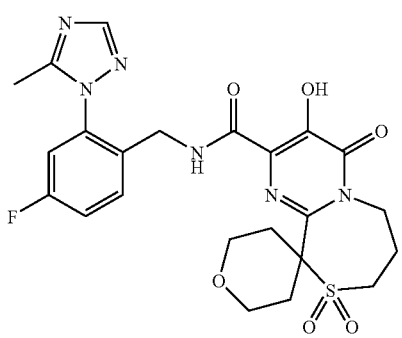

Spiro[4H-pyran-4,10'(4'H)-[6H]pyrimido[2,1-c][1,4]thiazepine]-2'-carboxamide, N-[[4-fluoro-2-(5-methyl-1H-1,2,4-triazol-1-yl)phenyl]methyl]-2,3,5,6,7',8'-hexahydro-3'-hydroxy-4'-oxo-, 9',9'-dioxide: Purple solid (0.0264 g, 92%; purity: 97%). $^1$H NMR (500 MHz, CDCl$_3$) δ: 12.50-11.02 (1H, br s), 8.23 (1H, t, J=6.1 Hz), 8.12 (1H, s), 7.71 (1H, dd, J=8.6, 5.8 Hz), 7.80 (1H, td, J=8.5, 2.4 Hz), 7.05 (1H, dd, J=8.2, 2.4 Hz), 4.48-4.47 (2H, br), 4.30 (2H, d, J=6.1 Hz), 4.08-4.01 (2H, m), 3.71-3.57 (2H, m), 3.42-3.33 (2H, m), 2.70-2.59 (4H, m), 2.57 (3H, s), 2.31-2.24 (2H, m). HRMS (M+H) calcd for $C_{23}H_{26}FN_6O_6S$: 533.1619. found: 533.1622.

I claim:
1. A compound of Formula I

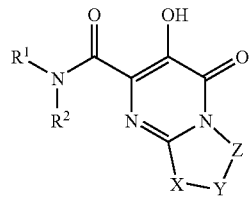

where:
$R^1$ is (Ar$^1$)alkyl, (Ar$^1$)(CON(R$^8$)(R$^9$))alkyl, (Ar$^1$)(CO$_2$R$^{14}$)alkyl, (Ar$^1$)hydroxyalkyl, or (Ar$^1$)oxyalkyl;

$R^2$ is hydrogen, alkyl, hydroxy, or alkoxy;

$R^3$ is hydrogen, halo, hydroxy, cyano, alkyl, cycloalkyl, $C_{5-7}$cycloalkenyl, haloalkyl, alkoxy, alkylthio, haloalkoxy, N(R$^8$)(R$^9$), NHAr$^2$, N(R$^6$)SO$_2$R$^7$, N(R$^6$)COR$^7$, N(R$^6$)CO$_2$R$^7$, OCOR$^7$, OCO$_2$R$^7$, OCON(R$^8$)(R$^9$), OCH$_2$CO$_2$R$^7$, OCH$_2$CON(R$^8$)(R$^9$), COR$^6$, CO$_2$R$^6$, CON(R$^8$)(R$^9$), SOR$^7$, S(=NR$^7$), SO$_2$R$^7$, SO$_2$N(R$^6$)(R$^6$), PO(OR$^6$)$_2$, C$_{2-4}$(R$^{12}$)alkynyl, R$^{13}$, Ar$^2$, or Ar$^3$;

$R^4$ is hydrogen, halo, hydroxy, cyano, alkyl, alkoxy, haloalkyl, haloalkoxy, or N(R$^6$)(R$^6$);

$R^5$ is hydrogen, halo, hydroxy, cyano, alkyl, alkoxy, haloalkyl, haloalkoxy, or N(R$^6$)(R$^6$);

$R^6$ is hydrogen, alkyl, or cycloalkyl;

$R^7$ is alkyl or cycloalkyl;

$R^8$ is hydrogen, alkyl, hydroxyalkyl, alkoxyalkyl or dialkylaminoalkyl;

$R^9$ is hydrogen, alkyl, hydroxyalkyl, alkoxyalkyl or dialkylaminoalkyl; or

N(R$^8$)(R$^9$) taken together is azetidinyl, pyrrolidinyl, (R$^{10}$)-piperidinyl, N—(R$^{11}$)-piperazinyl, morpholinyl, thiomorpholinyl, or dioxothiazinyl;

$R^{10}$ is hydrogen, alkyl, or hydroxyalkyl;

$R^{11}$ is hydrogen, alkyl, cycloalkyl, COR$^6$, or CO$_2$R$^6$;

$R^{12}$ is hydrogen, hydroxy, N(R$^6$)(R$^6$), SO$_2$R$^7$, OSO$_2$R$^7$, or dioxothiazinyl;

$R^{13}$ is azetidinonyl, pyrrolidinonyl, valerolactamyl, caprolactamyl, maleimido, oxazolidonyl, or dioxothiazinyl, and is substituted with 0-2 substituents selected from the group consisting of alkyl, hydroxyalkyl, acetoxyalkyl, and aminoalkyl;

$R^{14}$ is hydrogen or alkyl;

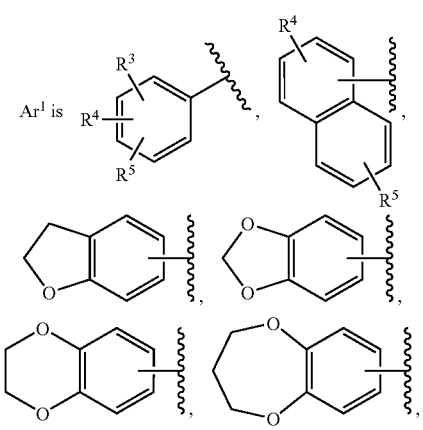

-continued

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, alkyl, alkoxy, $N(R^8)(R^9)$, $CON(R^8)(R^9)$, $CO_2R^6$, $CONHSO_2N(R^6)(R^6)$, $CONHSO_2N(R^6)$(phenyl), and $CONHSO_2N(R^6)$(halophenyl);

Ar³ is phenyl substituted with 0-2 substituents selected from the group consisting of halo, cyano, hydroxy, alkyl, alkoxy, alkoxyalkyl, haloalkyl, haloalkoxy, $N(R^8)(R^9)$, $CON(R^6)(R^6)$, and $CH_2N(R^8)(R^9)$, or is dioxolanylphenyl; and X-Y-Z is $C(R^{14})_2SC(R^{14})_2C(R^{14})_2$, $C(R^{14})_2SOC(R^{14})_2C(R^{14})_2$, or $C(R^{14})_2SO_2C(R^{14})_2C(R^{14})_2$;

or a pharmaceutically acceptable salt thereof.

2. A compound of claim 1 where
$R^1$ is (Ar¹)alkyl, (Ar¹)(CON($R^8$)($R^9$))alkyl, (Ar¹)(CO₂$R^{14}$)alkyl, (Ar¹)hydroxyalkyl, or (Ar¹)oxyalkyl;

$R^2$ is hydrogen, alkyl, hydroxy, or alkoxy;

$R^3$ is hydrogen, halo, hydroxy, cyano, alkyl, cycloalkyl, $C_{5-7}$cycloalkenyl, haloalkyl, alkoxy, alkylthio, haloalkoxy, $N(R^8)(R^9)$, NHAr², $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=NR^7)$, $SO_2R^7$, $SO_2N(R^6)(R^6)$, $PO(OR^6)_2$, $C_{2-4}(R^{12})$alkynyl, $R^{13}$, Ar², or Ar³;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, or cycloalkyl;

$R^7$ is alkyl or cycloalkyl;

$R^8$ is hydrogen, alkyl, hydroxyalkyl, alkoxyalkyl or dialkylaminoalkyl;

$R^9$ is hydrogen, alkyl, hydroxyalkyl, alkoxyalkyl or dialkylaminoalkyl; or $N(R^8)(R^9)$ taken together is azetidinyl, pyrrolidinyl,)($R^{10}$)-piperidinyl, N—($R^{11}$)-piperazinyl, morpholinyl, thiomorpholinyl, or dioxothiazinyl;

$R^{10}$ is hydrogen, alkyl, or hydroxyalkyl;

$R^{11}$ is hydrogen, alkyl, cycloalkyl, $COR^6$, or $CO_2R^6$;

$R^{12}$ is hydrogen, hydroxy, $N(R^6)(R^6)$, $SO_2R^7$, $OSO_2R^7$, or dioxothiazinyl;

$R^{13}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

$R^{14}$ is independently hydrogen or alkyl;

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, $C_{1-6}$alkoxy, $N(R^8)(R^9)$, $CON(R^8)(R^9)$, $CO_2R^6$, $CONHSO_2N(R^6)(R^6)$, $CONHSO_2N(R^6)$(phenyl), and $CONHSO_2N(R^6)$(halophenyl);

Ar³ is phenyl substituted with 0-2 substituents selected from the group consisting of halo, cyano, hydroxy, alkyl, alkoxy, alkoxyalkyl, haloalkyl, haloalkoxy, $N(R^8)(R^9)$, $CON(R^6)(R^6)$, and $CH_2N(R^8)(R^9)$, or is dioxolanylphenyl; and X-Y-Z is $C(R^{14})_2SC(R^{14})_2C(R^{14})_2$, $C(R^{14})_2SOC(R^{14})_2C(R^{14})_2$, or $C(R^{14})_2SO_2C(R^{14})_2C(R^{14})_2$;

or a pharmaceutically acceptable salt thereof.

3. A compound of claim 1 where $R^1$ is (Ar¹)alkyl.

4. A compound of claim 1 where $R^1$ is

5. A compound of claim 1 where $R^1$ is

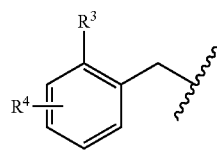

and $R^3$ is other than hydrogen or halo.

6. A compound of claim 1 where $R^2$ is hydrogen.

7. A compound of claim 1 where $R^3$ is $N(R^8)(R^9)$, $N(R^6)COR^7$, $OCON(R^8)(R^9)$, $CON(R^8)(R^9)$, $SOR^7$, $SO_2R^7$, $SO_2N(R^6)(R^6)$, $PO(OR^6)_2$, $R^{13}$, or $Ar^2$.

8. A compound of claim 1 where $R^3$ is $R^{13}$ or $Ar^2$.

9. A compound of claim 8 where $Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of halo and alkyl.

10. A compound of claim 1 where X-Y-Z is $C(R^{14})_2SCH_2CH_2$, or $C(R^{14})_2SO_2CH_2CH_2$.

11. A compound of claim 1 where X-Y-Z is $C(R^{14})_2SCH_2CH_2$, or $C(R^{14})_2SO_2CH_2CH_2$, and $R^{14}$ is other than hydrogen.

12. A compound of claim 1 according to one of the following structures

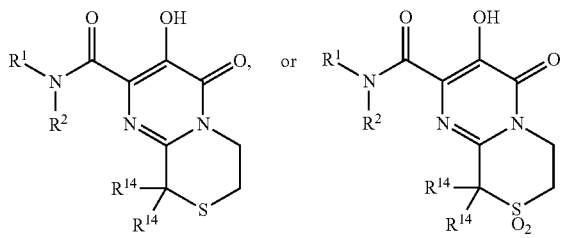

13. A compound of claim 12 where $R^{14}$ is other than hydrogen.

14. A compound of claim 12 where $R^{14}$ is methyl.

15. A compound of claim 1 selected from the group consisting of

N-(4-fluorobenzyl)-3-hydroxy-4-oxo-4,6,7,9-tetrahydro-pyrimido[2,1-c][1,4]thiazine-2-carboxamide;

Pyrimido[2,1-c][1,4]thiazine-2-carboxamide, N-[(4-fluorophenyl)methyl]-4,6,7,9-tetrahydro-3-hydroxy-4-oxo-, 8,8-dioxide;

Pyrimido[2,1-c][1,4]thiazine-2-carboxamide, N-[(4-fluorophenyl)methyl]-4,6,7,9-tetrahydro-3-hydroxy-9-methyl-4-oxo-, 8,8-dioxide;

Pyrimido[2,1-e][1,4]thiazine-2-carboxamide, N-[(4-fluorophenyl)methyl]-4,6,7,9-tetrahydro-3-hydroxy-9,9-dimethyl-4-oxo-, 8,8-dioxide;

Pyrimido[2,1-c][1,4]thiazine-2-carboxamide, N-[[4-fluoro-2-(1H-1,2,4-triazol-1-yl)phenyl]methyl]-4,6,7,9-tetrahydro-3-hydroxy-9,9-dimethyl-4-oxo-, 8,8-dioxide;

Pyrimido[2,1-c][1,4]thiazine-2-carboxamide, N-[[4-fluoro-2-(3-methyl-1H-1,2,4-triazol-1-yl)phenyl]methyl]-4,6,7,9-tetrahydro-3-hydroxy-9,9-dimethyl-4-oxo-, 8,8-dioxide;

Pyrimido[2,1-c][1,4]thiazine-2-carboxamide, N-[[4-fluoro-2-(5-methyl-1H-1,2,4-thiazol-1-yl)phenyl]methyl]-4,6,7,9-tetrahydro-3-hydroxy-9,9-dimethyl-4-oxo-8,8-dioxide;

or a pharmaceutically acceptable salt thereof.

16. A composition comprising a therapeutic amount of a compound of claim 1 and a pharmaceutically acceptable carrier.

17. A method for treating HIV infection comprising administering a therapeutically effective amount of a compound of claim 1, or a pharmaceutically acceptable salt thereof, to a patient.

* * * * *

UNITED STATES PATENT AND TRADEMARK OFFICE
CERTIFICATE OF CORRECTION

| | | |
|---|---|---|
| PATENT NO. | : 7,897,592 B2 | Page 1 of 2 |
| APPLICATION NO. | : 11/599580 | |
| DATED | : March 1, 2011 | |
| INVENTOR(S) | : B. Narasimhulu Naidu | |

It is certified that error appears in the above-identified patent and that said Letters Patent is hereby corrected as shown below:

In the Claims:

Claim 2:

Column 64, lines 7 to 14, change " 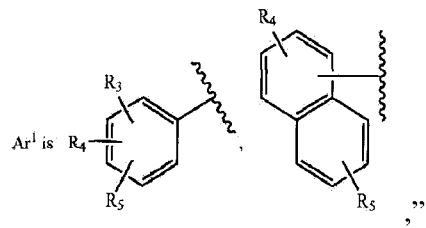 ,"

to -- $Ar^1$ is 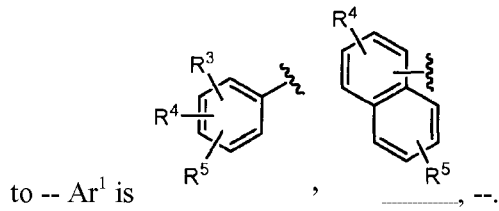, --.

Column 64, line 45, after "benzyl,", insert -- $C_{1-6}$alkyl, --.

Claim 12:

Column 65, line 32, after " 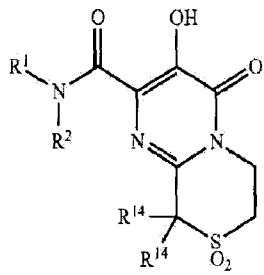 ", insert -- . --.

Signed and Sealed this
Twenty-seventh Day of December, 2011

David J. Kappos
*Director of the United States Patent and Trademark Office*

CERTIFICATE OF CORRECTION (continued)
U.S. Pat. No. 7,897,592 B2

Claim 15:

Column 66, line 15, change "[2,1-e]" to -- [2,1-c] --.